(12) United States Patent
Bates et al.

(10) Patent No.: US 8,343,536 B2
(45) Date of Patent: Jan. 1, 2013

(54) BIOFILM-INHIBITING MEDICAL PRODUCTS

(75) Inventors: Brian L. Bates, Bloomington, IN (US); Michael C. Hiles, Lafayette, IN (US); Chad E. Johnson, West Lafayette, IN (US)

(73) Assignees: Cook Biotech Incorporated, West Layfayette, IN (US); Cook Medical Technologies LLC, Bloomington, IN (US)

( * ) Notice: Subject to any disclaimer, the term of this patent is extended or adjusted under 35 U.S.C. 154(b) by 419 days.

(21) Appl. No.: 12/019,477

(22) Filed: Jan. 24, 2008

(65) Prior Publication Data

US 2008/0181950 A1  Jul. 31, 2008

Related U.S. Application Data

(60) Provisional application No. 60/897,114, filed on Jan. 24, 2007.

(51) Int. Cl.
*A61L 15/00* (2006.01)
*A61K 35/12* (2006.01)
*C12N 15/00* (2006.01)

(52) U.S. Cl. .................. 424/445; 424/520; 435/325

(58) Field of Classification Search .................. 424/445, 424/520; 435/325
See application file for complete search history.

(56) References Cited

U.S. PATENT DOCUMENTS

| | | | |
|---|---|---|---|
| 4,902,508 A | 2/1990 | Badylak et al. | |
| 5,052,381 A | 10/1991 | Gilbert et al. | |
| 5,275,826 A | 1/1994 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,445,833 A | 8/1995 | Badylak et al. | |
| 5,460,962 A | 10/1995 | Kemp | |
| 5,516,533 A | 5/1996 | Badylak et al. | |
| 5,554,389 A | 9/1996 | Badylak et al. | |
| 5,603,955 A | 2/1997 | Gehrke et al. | |
| 5,622,725 A | 4/1997 | Kross | |
| 5,641,518 A | 6/1997 | Badylak et al. | |
| 5,645,860 A | 7/1997 | Knapp, Jr. et al. | |
| 5,705,485 A | 1/1998 | Cini et al. | |
| 5,711,969 A | 1/1998 | Patel et al. | |
| 5,733,337 A | 3/1998 | Carr, Jr. et al. | |
| 5,753,267 A | 5/1998 | Badylak et al. | |
| 5,755,791 A | 5/1998 | Whitson et al. | |
| 5,762,966 A | 6/1998 | Knapp, Jr. et al. | |
| 5,788,625 A | 8/1998 | Plouhar et al. | |
| 5,885,619 A | 3/1999 | Patel et al. | |
| 5,922,028 A | 7/1999 | Plouhar et al. | |
| 5,928,671 A | 7/1999 | Domenico | |
| 5,955,110 A | 9/1999 | Patel et al. | |
| 5,968,096 A | 10/1999 | Whitson et al. | |
| 5,981,822 A | 11/1999 | Addison | |
| 5,993,844 A | 11/1999 | Abraham et al. | |
| 5,997,575 A | 12/1999 | Whitson et al. | |
| 6,086,921 A | 7/2000 | Domenico | |
| 6,096,347 A | 8/2000 | Geddes et al. | |
| 6,099,567 A | 8/2000 | Badylak et al. | |
| 6,126,686 A | 10/2000 | Badylak et al. | |
| 6,176,880 B1 | 1/2001 | Plouhar et al. | |
| 6,187,039 B1 | 2/2001 | Hiles et al. | |
| 6,206,931 B1 | 3/2001 | Cook et al. | |
| 6,248,371 B1 | 6/2001 | Domenico | |
| 6,331,319 B1 | 12/2001 | Badylak et al. | |
| 6,346,391 B1 | 2/2002 | Oethinger et al. | |
| 6,358,284 B1 | 3/2002 | Fearnot et al. | |
| 6,379,710 B1 | 4/2002 | Badylak | |
| 6,380,248 B1 | 4/2002 | Domenico et al. | |
| RE37,793 E | 7/2002 | Domenico | |
| 6,447,798 B1 | 9/2002 | Munro et al. | |
| 6,468,521 B1 | 10/2002 | Pedersen et al. | |
| 6,566,577 B1 | 5/2003 | Addison et al. | |
| 6,572,650 B1 | 6/2003 | Abraham et al. | |
| 6,582,719 B2 | 6/2003 | Modak et al. | |
| 6,635,272 B2 | 10/2003 | Leaderman | |
| 6,800,278 B1 | 10/2004 | Perrault et al. | |
| 7,094,394 B2 | 8/2006 | Davies et al. | |
| 7,094,431 B2 | 8/2006 | Peshoff | |
| 7,147,871 B2 * | 12/2006 | Voytik-Harbin et al. | ..... 424/551 |
| 7,244,444 B2 | 7/2007 | Bates | |
| 2001/0043943 A1 | 11/2001 | Coffey | |
| 2002/0103542 A1 | 8/2002 | Bilbo | |
| 2003/0013989 A1 | 1/2003 | Obermiller et al. | |

(Continued)

FOREIGN PATENT DOCUMENTS

GB  1526778  9/1978

(Continued)

OTHER PUBLICATIONS

Zhang et al., Inhibitionof Bacterial Adherance on the Surface of Stents and Bacterial Grouwth in Bile by Bismuth Dimercaprol, Jun. 2005, Digestive diseases and Sciences, vol. 50, No. 6, pp. 1046-1051.*
Domenico, Philip et al., BisEDT and RIP act in synergy to prevent graft ingections by resistant staphylococci, 2004, Peptides, vol. 25, pp. 2047-2053.*
Bradley, M. et al., Systematic reviews of wound care management: (2) Dressings and topical agents used in the healing of chronic wounds, *Health Technology Assessment*, vol. 3, No. 17 (Pt. 2), (1999).
Bradley, M. et al., The debridement of chronic wounds: a systematic review, *Health Technology Assessment*, vol. 3, No. 17 (Pt. 1), (1999).
Bruns and Worthington (2000) Am. Fam. Physician 61:1383-1388.
Carmeliet, P., Mechanisms of angiogenesis and arteriogenesis, Nat Med 6 (2000), No. 4, 389-395.
Cullum, N. et al., Systematic reviews of wound care management: (5) beds; (6) compres-sion; (7) laser therapy and electromagnetic therapy, *Health Technology Assessment*, vol. 5, No. 9, (2001).
Davey, M. E. et al., Microbial Biofilms: from Ecology to Molecular Genetics, *Microbiology and Molecular Biology Reviews*, vol. 64, No. 4, p. 847-867, (Dec. 2000).

(Continued)

Primary Examiner — Lezah Roberts
Assistant Examiner — Nannette Holloman
(74) Attorney, Agent, or Firm — Brinks Hofer Gilson & Lione

(57) ABSTRACT

A biofilm-inhibiting medical product includes a carrier formed from a natural, bioremodelable material, whereby the carrier includes a biocidal bismuth thiol agent and/or one or more other biofilm-inhibiting or wound healing agents. A method for using the biofilm-inhibiting medical product to treat a wound or tissue defect in a patient's body is described.

16 Claims, 2 Drawing Sheets

U.S. PATENT DOCUMENTS

| | | |
|---|---|---|
| 2003/0023316 A1 | 1/2003 | Brown et al. |
| 2003/0035848 A1 | 2/2003 | Batarseh et al. |
| 2003/0065292 A1 | 4/2003 | Darouiche et al. |
| 2003/0153983 A1 | 8/2003 | Miller et al. |
| 2004/0005350 A1 | 1/2004 | Looney et al. |
| 2004/0120993 A1 | 6/2004 | Zhang et al. |
| 2004/0180042 A1 | 9/2004 | Cook et al. |
| 2004/0230177 A1 | 11/2004 | DiMatteo et al. |
| 2005/0013870 A1 | 1/2005 | Freyman et al. |
| 2005/0021141 A1 | 1/2005 | Bleyer et al. |
| 2005/0027307 A1 | 2/2005 | Schwartz et al. |
| 2005/0158263 A1 | 7/2005 | Rioux et al. |
| 2005/0249772 A1 | 11/2005 | Malaviya et al. |
| 2005/0256437 A1 | 11/2005 | Silcok et al. |
| 2005/0260251 A1 | 11/2005 | Hiltner et al. |
| 2005/0273155 A1 | 12/2005 | Bahler et al. |
| 2006/0014285 A1 | 1/2006 | Eldridge et al. |
| 2006/0040894 A1 | 2/2006 | Hunter et al. |
| 2006/0045899 A1 | 3/2006 | Sarangapani |
| 2006/0193885 A1 | 8/2006 | Neethling et al. |
| 2006/0201996 A1 | 9/2006 | Hodde |
| 2006/0251702 A1 | 11/2006 | Janis et al. |
| 2007/0088445 A1 | 4/2007 | Patel et al. |
| 2007/0141101 A1* | 6/2007 | Nugent et al. ................ 424/423 |
| 2007/0184122 A1 | 8/2007 | Johnson et al. |
| 2008/0004657 A1 | 1/2008 | Obermiller et al. |

FOREIGN PATENT DOCUMENTS

| | | |
|---|---|---|
| WO | WO 98/22158 | 5/1998 |
| WO | WO 98/58075 | 12/1998 |
| WO | WO 99/21568 | 5/1999 |
| WO | WO 99/39707 | 8/1999 |
| WO | WO 00/07638 | 2/2000 |
| WO | WO 00/33895 | 6/2000 |
| WO | WO 00/71139 A2 | 11/2000 |
| WO | WO 03/002165 A1 | 1/2003 |
| WO | WO 03/011821 A2 | 2/2003 |
| WO | WO 03/035125 A2 | 5/2003 |
| WO | WO 03/045294 A1 | 6/2003 |
| WO | WO 03/066119 A1 | 8/2003 |
| WO | WO 2004/103071 A1 | 12/2004 |
| WO | WO 2005/018701 A1 | 3/2005 |
| WO | WO 2005/020847 A2 | 3/2005 |
| WO | WO 2005/030186 A2 | 4/2005 |
| WO | WO 2005/055723 A1 | 6/2005 |
| WO | WO 2005/087135 A2 | 9/2005 |
| WO | WO 2005/094579 A1 | 10/2005 |
| WO | WO 2005/097219 A2 | 10/2005 |
| WO | WO 2005/107455 A2 | 11/2005 |
| WO | WO 2006/031554 A2 | 3/2006 |
| WO | WO 2006/044512 A1 | 4/2006 |
| WO | WO 2006/045041 A2 | 4/2006 |
| WO | WO 2006/121887 A2 | 11/2006 |
| WO | WO 2008/067085 A2 | 6/2008 |

OTHER PUBLICATIONS

Domenico, Philip et al., Activities of Bismuth Thiols against Staphylococci and Staphylococcal Biofilms, *Antimicrobial Agents and Chemotherapy*, vol. 45, No. 5, p. 1417-1421 (May 2001).

Domenico, Philip et al., Enhancement of Bismuth Antibacterial Activity with Lipophilic Thiol Chelators, *Antimicrobial Agents and Chemotherapy*, vol. 41, No. 8, p. 1697-1703 (Aug. 1997).

Domenico, Philip et al., Surface Antigen Exposure by Bismuth Dimercaprol Suppression of *Klebsiella pneumonia* Capsular Polysaccharide, *Infection and Immunity*, vol. 67, No. 2, p. 664-669 (Feb. 1999).

Donlan, Rodney M., et al., Biofilms: Survival Mechanisms of Clinically Relevant Microorganisms, *Clinical Microbiology Reviews*, vol. 15, No. 2, p. 167-193 (Apr. 2002).

Drosou, Anna, MD, et al., Feature: Antiseptics on Wounds: An Area of Controversy (Part One), *Wounds* vol. 15, Issue 5, p. 149-166 (May 2003).

Drosou, Anna, MD, et al., Feature: Antiseptics on Wounds: An Area of Controversy (Part Two), *Wounds*, vol. 15, Issue 5, p. 149-166 (May 2003).

Gilbert, Peter et al., Potential Impact of Increased Use of Biocides in Consumer Products on Prevalence of Antibiotic Resistance, *Clinic Microbiology Reviews*, vol. 16, No. 2, p. 189-208 (Apr. 2003).

Harding, K.G. et al., Healing chronic wounds, *BMJ* vol. 324, p. 160-3, (Jan. 19, 2002).

Heeschen, C. et al., Nat Med vol. 7, No. 7, pp. 833-839, 2001.

Huynh, Nature Biotechnology, vol. 17, p. 1083-1086 (Nov. 1999).

International Search Report Jul. 28, 2009.

Johansen, Charlotte et al., Enzymatic Removal and Disinfection of Bacterial Biofilms, *Applied and Environmental Microbiology*, vol. 63, No. 9, p. 3724-3728 (Sep. 1997).

Johnson, C. et al.,Matrix Metalloproteinase-9 Is Required fro Adequate Angiogenic Revascularization of Ischemic Tissues: Potential Role in Capillary Branching, *Circ Res.*, vol. 94, No. 2, pp. 262-268, 2004.

Jugdutt, Bodh I., Ventricular Remodeling After Infarction and the Extracellular Collagen Matrix: When Is Enough Enough?, *Circulation*, 108; p. 1395-1403, (2003).

Lobmann, Ralf, MD, et al., Proteases and the Diabetic Foot Syndrome: Mechanisms and Therapeutic Implications, *Diabetes Care*, vol. 28, No. 2 (Feb. 2005).

MedPro Month (1999) 9:261-262.

MedPro Month (2000) 10:86-91.

Mertz, Patricia M., Cutaneous Biofilms: Friend or Foe?, *Wounds* 15(5): p. 129-132, (2003).

Monami, M. et al., Use of an Oxidized Regenerated Cellulose and Collagen Composite for Healing of Chronic Diabetic Foot Ulcers, *Diabetes Care*, vol. 25, No. 10, (Oct. 2002).

Munro, Neil et al., Infections in the diabetic foot, A practical management guide to foot care, *The British Journal of Diabetes and Vascular Disease*, vol. 3, Issue 2, p. 132-6, (Mar./Apr. 2003).

O'Gara, James et al., *Staphylococcus epidermidis* biofilms: importance and implications, *J. Med. Microbiol.*, vol. 50, p. 582-587 (2001).

O'Meara, S. et al., Systematic reviews of wound care management: (3) antimicrobial agents for chronic wounds; (4) diabetic foot ulceration, *Health Technology Assessment*, vol. 4, No. 21 (2000).

Ryder, Marcia A, Catheter-Related Infections: It's All About Biofilm, *Topics in Advanced Practice Nursing* 5(3) (Posted Aug. 18, 2005).

Scardillo, J. Managing tubes and drains: Considerations for infection control, *Infection Control Resource*, vol. 2, No. 1, p. 2-3, 6-7, (2003).

Steffensen, Bjorn et al., Proteolytic Events of Wound-Healing—Coordinated Interactions Among Matrix Metalloproteinases (MMPs), Integrins, and Extracellular Matrix Molecules, *Crit Rev Oral Biol Med*, 12(5), p. 373-398 (2001).

Tapiainen, Terhi et al., Ultrastructure of *Streptococcus pneumonia* after exposure to xylitol, *Journal of Antimicrobial Chemotherapy*, 54, p. 225-228 (2004).

Tomaselli, Nancy, Prevention and treatment of surgical-site infections, *Infection Control Resource*, vol. 2, No. 1, p. 1, 4-6, (2003).

Veloira, W. G. et al., In vitro activity and synergy aof bismuth thiols and tobramycin against Burkholderia cepacia complex, *J. Antimicrobial chemotherapy*, 52, p. 915-919, (2003).

Wu, Chieh-Liang et al., Subinhibitory Bismuth-Thiols Reduce Virulence of *Pseudomonas aeruginosa*, *Am. J. Respir. Cell. Mol. Biol.*, vol. 26, p. 731-738 (2002).

Zhang et al.; *Digestive Diseases and Sciences*, vol. 50, No. 6 (Jun. 1, 2006) pp. 1046-1051.

* cited by examiner

BIOFILM-INHIBITING MEDICAL PRODUCTS

This application claims the benefit of priority under 35 U.S.C. §119(e) to U.S. Provisional Application No. 60/897,114, filed Jan. 24, 2007, which is hereby incorporated by reference in its entirety.

TECHNICAL FIELD

This invention is directed to biofilm-inhibiting medical products (e.g., wound dressings) including a carrier formed from a natural, bioremodelable material, the carrier including a biocidal bismuth thiol agent and/or one or more other biofilm-inhibiting or wound healing agents. This invention is also directed to methods of using the medical product for treating a tissue defect in a patient's body.

BACKGROUND

A biofilm is a community of sessile, stably attached microorganisms, especially bacteria, embedded in a hydrated matrix of extracellular polymeric substances exhibiting growth properties that are distinguished from those of planktonic, free-living microorganisms. Biofilms represent a target of new compositions for inhibiting, reducing, preventing, and removing microbial infections, and are believed to be partly responsible for increasing the rates of antibiotic resistance. It is thought that upwards of 60% of all nosocomial (hospital-derived) infections are due to biofilms, whose role in contaminating medical implants is now well established. Central venous catheters (CVCs) pose the greatest risk of device-related infections with infection rates of 3 to 5% and account for the most serious and costly healthcare-associated infections (See for example, Donlan and Costerton, Clin. Microbiol. Rev., Vol. 15, No. 2, pp. 167-193, 2002; Davey and O'Toole, Microbiol. Mol. Biol. Rev., Vol. 64, No. 4, pp. 847-867, 2000).

One approach to managing biofilm infections is to identify the microorganism(s) in the biofilm and to find antibiotic or biocidal agents capable of killing the microorganisms. A major limitation of this approach is that models for testing the efficacy of these agents to not sufficiently represent a biofilm environment. Biofilm bacteria can be up to 1,000-fold more resistant to antibiotic treatment than the same organism grown planktonically. Biofilm bacteria are also more resistant to biocides, such as peroxide, bleach, acids, and other biocidal agents.

In spite of the dramatic differences in susceptibility to antimicrobial agents between planktonic and sessile, biofilm microorganisms, current approaches for targeting biofilm microorganisms are insufficient in addressing this discrepancy. Antimicrobial efficacy testing often employs standard broth microdilution methods reflecting antibiotic efficacy in planktonic, rather than biofilm systems. Accordingly, broad numbers of prospective antibiotic- and biocidal agents have been identified without any expectation of success in the more "real" biofilm world.

The mechanisms by which resistance to antibiotic or biocidal agents is achieved remain subject to speculation. It is now known, however, that the structural organization of biofilms hinders the ability of antibiotics or biocides to access biofilm bacteria and can protect bacteria from a host's immune system. Clinical biofilm infections are marked by recurring symptoms after repeated antibody treatments. Such treatments typically eliminate planktonic microorganisms, but allow sessile, biofilm microorganisms to propagate and disseminate upon termination of antibiotic therapy.

In recent years, biofilm-based infections attributed to medical devices, such as catheters, prosthetic heart valves, contact lenses, and intrauterine devices have received increased attention. Despite circumstantial evidence suggesting biofilms to be a major culprit responsible for chronic wounds, their role in chronic wounds remains poorly understood.

Chronic wounds are open wounds that are recalcitrant to healing. Chronic wounds are painful, diminish the quality of life, impair mobility, and frequently lead to amputations. And they present an enormous financial toll worldwide. In 2004, diabetic foot ulcers accounted for $10 billion in direct costs (about 4% of the total personal health spending) and another $5 billion in indirect costs (disability, nursing homes, etc.). In the U.S., chronic wounds affect roughly 3 million people and are increasing at exponential rates, doubling every 4-5 years.

Chronic wounds have a number of barriers which limit healing. Many of these barriers have been extensively studied, including poor perfusion, white cell dysfunction, poor nutrition, and repetitive pressure among others. Although wound beds are known to be populated by biofilms, their role in abrogating or delaying wound healing has not yet been experimentally established. In addition, there are questions regarding the extent to which the cellular regeneration processes accompanying the healing may inadvertently provide nutritional support for sustaining biofilm viability.

In light of the foregoing, including the ongoing problems with conventional wound healing treatments, there is a need for improved compositions and methods for treating chronic wound bed biofilms and for adequately balancing the tissue regeneration demands necessary for achieving full and timely healing wounds, particularly chronic wounds.

SUMMARY

In one aspect, a wound dressing or other medical product includes a carrier formed from a natural, bioremodelable material, whereby the carrier further includes, and is formulated to deliver, a biocidal bismuth thiol agent and/or other biofilm-inhibiting or wound healing agents. In a preferred embodiment the carrier is formed from extracellular matrix (ECM) material and the bismuth thiol is bismuth-1,2-ethanedithiol.

In another aspect, a method of making a wound dressing or other medical product includes providing a carrier in the form of a natural, bioremodelable material and incorporating a bismuth thiol into or onto at least a portion of the carrier.

In a further aspect, a method of treating a wound or other bodily defect includes contacting a wound or other site in need of treatment with a wound dressing or medical product of the present invention. In one preferred embodiment, the method includes treatment of a chronic wound with a wound dressing containing a bismuth dithiol and/or one or more other biofilm-inhibiting or wound healing agents.

In another aspect, a hernia repair device and method are provided. The hernia repair device includes a sheet of a natural, bioremodelable material. The device further includes, and is formulated to deliver, a biocidal bismuth thiol agent. In a preferred embodiment the device comprises at least one extracellular matrix (ECM) material, and the bismuth thiol is bismuth-1,2-ethanedithiol.

When applied to a wound or other tissue defect, the dressing enhances treatment by preventing or reducing biofilm formation or development. Whereas biofilm-inhibiting agents serve to prevent, reduce, and/or eliminate biofilm microorganisms in a wound, the bioremodelable matrix provides a material source to promote wound healing and tissue rebuilding. In particular, the bioremodelable ECM materials provide a rapidly vascularized matrix to promote the remodeling and regrowth of endogenous tissue, which ultimately replaces the exogenously provided ECM-based material.

In the present invention, it is believed that the use of bismuth thiols in conjunction with bioremodelable materials significantly improves management of chronic wounds and other tissue defects. Moreover, it is believed that the use of bismuth thiols together with other biofilm-inhibiting- and/or wound healing agents can provide synergistic benefits when treating chronic wounds and other tissue defects. While not wishing to be bound by theory, it is believed that the biofilm-inhibiting substances of the present invention promote the wound-healing process by obviating the negative consequences of wound bed biofilms on the wound- or defect-healing process. It is further believed that when used in combination with bioremodelable ECM materials, a further enhancement in healing can be achieved.

In view of the advantageous properties of the medical products of this invention, it is believed that treatment times can be reduced, as well as the need for repeated debridement of the tissue defect area.

DETAILED DESCRIPTION

Figure 1:
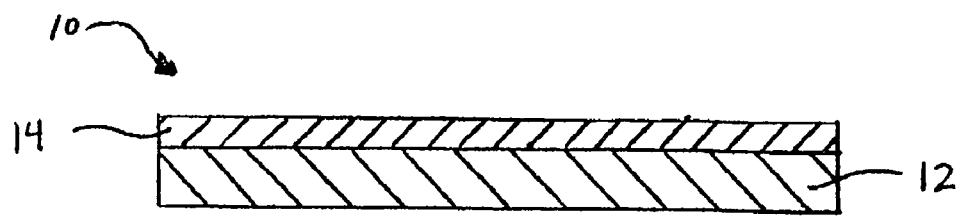
FIG. 1 is a schematic illustration of a medical device construct in accordance with the present invention.

It is also to be understood that the terminology used herein is for the purpose of describing particular embodiments only, and is not intended to limit the scope of the present invention which will be limited only by the appended claims. It must be noted that as used herein and in the appended claims, the singular forms "a," "an," and "the" include plural reference unless the context clearly dictates otherwise. Thus, for example, reference to "a cell" is a reference to one or more cells and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein may be used in the practice or testing of the invention, the preferred methods, devices and materials are now described.

Definitions of Terms

As used herein, the term "wound" denotes a bodily injury with disruption of the normal integrity of tissue structures. The term is also intended to encompass the terms "sore", "lesion", "necrosis" and "ulcer". The term "sore" typically refers to any lesion of the skin or mucous membranes. The term "ulcer" refers to a local defect, or excavation, of the surface of an organ or tissue, which is produced by the sloughing of necrotic tissue. The term "lesion" relates to any tissue defect. The term "necrosis" relates to dead tissue resulting from infection, injury, inflammation or infarctions.

The term "chronic wound" denotes a wound not healed or typically not healed after 4 to 6 weeks of conventional treatment.

The term "biofilm" denotes an extracellular matrix in which microorganisms are dispersed and/or form colonies. The biofilm typically is made of polysaccharides and other macromolecules. In addition, in the present invention, the phrase "inhibiting a biofilm," and like phrases, means the prevention of biofilm growth, reduction in the rate of biofilm growth, partial eradication of existing biofilm, and/or complete eradication of existing biofilm.

The term "biocidal" is art recognized and includes broad spectrum acting agents believed by those of ordinarily skill in the art prior to the present invention to kill microbial cells "non-specifically" by modes of action affecting a plurality of different targets. Examples of biocidal agents include bismuth thiols, paraben, chlorobutanol, phenol, alkylating agents such as ethylene oxide and formaldehyde, halides, mercurials and other heavy metals, detergents, acids, alkalis, disinfectants, pine oil, triclosan, quaternary amine compounds such as alkyl dimethyl benzyl ammonium chloride, chloroxylol, chlorhexidine, and cyclohexidine, and triclocarbon.

The term "antibiotic" is art recognized and includes antimicrobial agents synthesized by an organism, isolated from the natural source, and includes natural or chemically synthesized analogs thereof. The term includes but is not limited to: polyether ionophore such as monensin and nigericin; macrolide antibiotics such as erythromycin and tylosin; aminoglycoside antibiotics such as streptomycin and kanamycin; beta-lactam antibiotics such as penicillin and cephalosporin; and polypeptide antibiotics such as subtilisin and neosporin. In contrast to the term "biocidal," an antibiotic is considered to have a specific molecular target in a microbial cell.

The term "bactericidal" refers to an agent that can kill a bacterium; "bacteriostatic" refers to an agent that inhibits the growth of a bacterium.

The term "quorum sensing signaling" or "quorum sensing" denotes generation of a cellular signal in response to cell density. In one embodiment, quorum sensing signaling mediates the coordinated expression of specific genes.

The term "quorum sensing controlled gene" denotes a gene whose expression is regulated in a cell density dependent fashion. A quorum sensing controlled gene may encode a protein or polypeptide that, either directly or indirectly, inhibits and/or antagonizes a bacterial host defense mechanism or that regulates biofilm formation.

The term "quorum sensing signal molecule" denotes a molecule that transduces a quorum sensing signal and mediates the cellular response to cell density. The quorum sensing signal molecule may regulate expression of the quorum sensing controlled gene. Exemplary quorum sensing signal molecules include freely diffusible autoinducer molecules, such as homoserine lactone molecules or analogs thereof.

The term "bioremodelable" refers to a natural or synthetic material capable of inducing tissue remodeling in a subject or host. A bioremodelable material can include at least one bioactive agent (e.g., growth factor, etc.) capable of inducing tissue remodeling. The ability to induce tissue remodeling may be ascribed to one or more bioactive agents in a bioremodelable material stimulating the infiltration of native cells into an a cellular matrix, stimulating new blood vessel formation (capillaries) growing into the matrix to nourish the infiltrating cells (angiogenesis), and/or effecting the degradation and/or replacement of the bioremodelable material by endogenous tissue. The bioremodelable material may include extracellular collagen matrix (ECM) material, including but not limited to submucosal tissue, such as small intestine submucosal (SIS) tissue or it may include other natural tissue source materials, or other natural or synthetic materials, including one or more bioactive substances capable of inducing tissue remodeling.

The terms "angiogenesis and angiogenic" refer to bioremodelable properties defined by formation of capillaries or microvessels from existing vasculature in a process necessary for tissue growth, where the microvessels provide transport of oxygen and nutrients to the developing tissues and remove waste products.

The term "submucosa" refers to a natural collagen-containing tissue structure removed from a variety of sources including the alimentary, respiratory, intestinal, urinary or genital tracts of warm-blooded vertebrates. Submucosal material according to the present invention includes tunica submucosa, but may include additionally adjacent layers from the source tissue, such as the lamina muscularis mucosa and the stratum compactum, the lamina propria and/or other tissue structures. It will be understood that the submucosal material may include all or only a portion of the original tunica submucosa of a source tissue, considered in terms of thickness and/or width of the original tunica submucosa. A submucosal material may be a decellularized or acellular tissue, which means it is devoid of intact viable cells, although some cell components may remain in the tissue following purification from a natural source. Alternative embodiments (e.g., fluidized compositions etc.) include submucosal material expressly derived from a purified submucosal matrix structure. Submucosal materials according to the present disclosure are distinguished from collagen materials in other medical devices that do not retain their native submucosal structures or that were not prepared from purified submucosal starting materials first removed from a natural submucosal tissue source.

The term "small intestinal submucosa" (SIS) refers to a particular type of submucosal structure removed from a small intestine source, such as pig.

The term "biocompatible" refers to something, such as certain types of extracellular matrix material, that can be substantially non-toxic in the in vivo environment of its intended use, and is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "therapeutically effective amount" refers to an amount of a modulator, drug or other molecule that is sufficient to effect treatment when administered to a subject in need of such treatment. A therapeutically effective amount will vary depending upon the subject and disease condition being treated, the weight and age of the subject, the severity of the disease condition, the manner of administration and the like.

The term "carrier" refers to a natural or synthetic material carrying and delivering one or more exogenously added bioactive agents, including bismuth thiol agents, such as bismuth-1,2-ethandithiol; other biofilm-inhibiting agents, such as lactoferrin, xylitol, quorum sensing inhibitors, biocidal agents, antibiotics, and surfactants; wound healing agents, such as growth factors, cytokines, and protease inhibitors; analgesic agents, and the like.

The term "gel" refers to a three-dimensional polymer network that includes a liquid solvent entrained by an interconnected matrix of polymer chains. More particularly, the term refers to polymer networks between the liquid and solid state containing enough solvent molecules to cause macroscopic changes in the sample dimension. The term is also meant to include gels in their "dry" condition, in which all substantially all solvent that is within the gel matrix has been removed. The term dry is primarily an operational definition. One definition of the term is when the mass of the gel reaches a constant low value in desiccator or drying oven.

The terms "patient," "subject," and "recipient" as used in this application refer to any mammal, especially humans. For purposes of treatment, the term "mammal" refers to any animal classified as a mammal, including humans, domestic and farm animals, and zoo, sports, or pet animals, such as dogs, horses, cats, cattle, pigs, sheep, etc. Preferably, the mammal is human.

In one aspect, a wound dressing, graft material or other medical product includes a carrier formed from natural, bioremodelable material, whereby the carrier further includes or is formulated to deliver, a biocidal bismuth thiol agent and/or other biofilm-inhibiting- or wound healing agents. In a preferred embodiment the carrier is formed from extracellular matrix (ECM) material, and the bismuth thiol is bismuth-1,2-ethanedithiol.

When applied to a wound, the dressing enhances wound treatment by preventing or reducing biofilm formation or development. The bioremodelable matrix provides a material source to promote wound healing and tissue rebuilding. For example, when placed over a wound, the bioremodelable ECM materials provide a rapidly vascularized matrix to support the growth and remodeling of new endogenous tissue, and the biofilm-inhibiting agents serve to reduce or prevent biofilm formation and development to enhance wound treatment.

Wound dressings or other medical products of the present invention employ carriers which may be applied in a variety of forms, including single- or multi-layer sheet constructs, fluidized formulations, and/or combinations thereof. Sheet constructs or fluidized formulations may be made from bioremodelable ECM-based materials. The sheet or fluidized carrier materials may be further formed into a suitable 3-D structure, such as a plug or wedge or applied in a dried powdered form. A bismuth thiol containing ECM material can be used in the treatment of a fistula, including a fistula having an opening into the gastrointestinal tract such as an anorectal fistula, enterocutaneous fistula, a rectovaginal fistula, or others. For these purposes, the ECM material can be processed into the form of a plug or other shape to occlude at least the primary opening of the fistula, as disclosed for example in United States Patent Application Publication No. 2008/0004657 dated 3 Jan. 2008 and United States Patent Application Publication No. 2007/0088445 dated Apr. 19, 2007, each of which is hereby incorporated herein by reference in its entirety.

Additional biocompatible substrate films or layers may be included in conjunction with the carrier, including a top sheet to restrict passage of liquid back towards the wound or defect; a backing layer providing a barrier to passage of microorganisms through the dressing; an absorbent layer for absorbing wound fluids; and/or an adhesive layer forming an adhesive-coated margin.

Wound dressings of the present invention may be used to manage a variety of wounds, including partial and full thickness wounds, diabetic ulcers, venous ulcers, chronic vascular ulcers, leg ulcers, pressure ulcers, decubitus, ulcus cruris, tunneled/undermined wounds, fistulae, surgical wounds (such as donor site wounds for autografts, post-Moh's surgery wounds, post-laser surgery wounds, wound dehiscence), trauma wounds (such as abrasions, lacerations, second-degree burns, and skin tears), and draining wounds.

Graft materials or graft products of the invention can find wide use in the field of medicine, and in this regard, can be adapted to provide a variety of devices and objects suitable for application to and/or implantation within a patient. The present invention also provides, in certain aspects, various methods for using these materials, for example, to replace, augment, repair, and/or otherwise suitably treat diseased or otherwise damaged or defective tissue of a patient. Illustratively, graft materials of the invention can be configured as implantable devices suitable for bulking tissue, providing hemostasis, and/or providing occlusion in a passageway or other open space within the body of a patient (e.g., as an embolization device, fistula plug, etc.). In some embodiments, graft materials of the invention are configured as single- or multilayered patches or other sheet or sheet-like devices for providing support to patient tissue or otherwise treating patient tissue. Illustratively, inventive graft materials can provide wound healing products suitable for cutaneous, intracutaneous, and/or subcutaneous wound treatment, e.g., a hernia repair patch or a burn treatment material. As well, sheet-form graft products of the invention find use as precursor materials for forming a variety of other medical devices, or components thereof. Illustratively, graft materials of the invention can be processed into various shapes and configurations, for example, into a urethral sling or a prosthetic body part. In some forms, sheet-form graft materials of the invention are suitable for forming tubular grafting devices, which may be used to replace a circulation vessel, or a portion thereof, or to bypass a blocked vessel.

In one preferred embodiment, medical products, including graft materials in accordance with the present invention can be used as tissue grafts in mammalian patients, including humans. Graft materials in accord with certain embodiments of the invention can be useful in the repair or support of soft tissue areas, such as body walls. The graft products or graft materials can include any of the carrier formulations or medical device constructs described herein for internal or external grafting. For example, in illustrative embodiments, graft materials of the invention can be used in hernia repair applications. Such applications include the repair of a hiatal hernia by affixing or securing the graft product over or near a tear in the esophageal hiatus of the diaphragm. The graft product can be fastened or secured to the esophageal hiatus by placing sutures and/or staples, and/or other suitable fasteners and/or the like, through the reinforcement bands in the graft product and into the esophageal hiatus.

In alternative embodiments, graft products of the invention can be used in the repair or support of tissue surrounding an inguinal hernia by affixing a graft product of this invention over and/or near to a tear in the abdominal wall in the groin region. Again, the graft product can be attached to the soft tissue of the abdominal wall by placing sutures, and/or staples, and/or other fasteners through the reinforcement band or bands present in the graft product and into the tissue wall. In addition to repairing inguinal hernias, the present invention may also include implantable grafts suitable for other types of body wall reinforcement or repair. Further examples of implantable grafts include slings configured to prevent prolapse of a particular pelvic organ, such as the urethra, bladder, rectum, or small bowel.

As indicated above, wound dressings, graft materials or other medical products of the present invention include a biocidal bismuth thiol agent and a carrier. The carrier includes a natural, bioremodelable material, preferably an extracellular matrix (ECM) material, such as submucosal tissue material in solid or fluidized form.

FIG. 1 is a schematic illustration of medical device construct or medical device 10 (such as wound dressing) including an ECM material layer 12, where bismuth thiols 14 are applied by coating onto at least one side of the ECM material layer 12. The medical device construct 10 may be applied to a tissue directly or it may be attached to or incorporated into another medical device or product.

The carrier may further include other biofilm-inhibiting agents, wound healing agents, and/or analgesic agents. One or more of these agents may be exogenously incorporated into the carrier during their preparation or covalently attached to the carrier when preparing the wound dressing or other medical product. Alternatively, the biofilm-inhibiting and/or wound healing agents may be added to the carrier after preparation of the carrier, e.g., by coating, soaking, spraying, painting, or otherwise applying the biofilm-inhibiting and/or wound healing agent(s) to the carrier.

In another aspect, the carrier includes fluidized ECM materials formulated as a substantially homogenous biofilm-inhibiting solution containing bismuth thiols and/or other exogenously added bioactive agents. Fluidized ECM materials may be dried or formed into a gel or foam for direct application to a wound-contacting layer or tissue defect further utilized in a composite wound dressing including one or more biocompatible substrate layers. The resulting multilayer construct may be dried by lyophilization.

Figure 2:
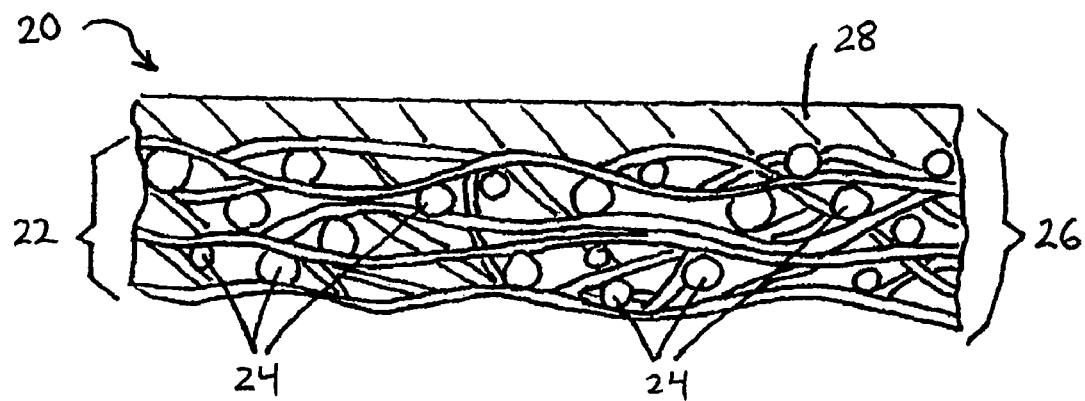
FIG. 2 is a schematic illustration of a medical device construct according to another aspect of the present invention.

FIG. 2 is a schematic illustration of an exemplary medical device construct 20 including an ECM material layer 22 where bismuth thiols 24 are incorporated into the ECM material layer 22 by mixing the bismuth thiols 24 into a fluidized ECM solution and allowing the resultant solution to dry in the form of a dried cake 26. The dried cake 26 may be used as a medical device (e.g. a wound dressing) by itself or it may be attached or incorporated into another medical device or product. Alternatively, other biofilm-inhibiting agents may be additionally added to aid in the repair, replacement, treatment, and/or healing of a wound. The additional biofilm-inhibiting agents may be added to the surface of the dried cake 26 as a layer 28 or they may be incorporated into the fluidized ECM solution prior to forming the dried cake 26.

Figure 3:
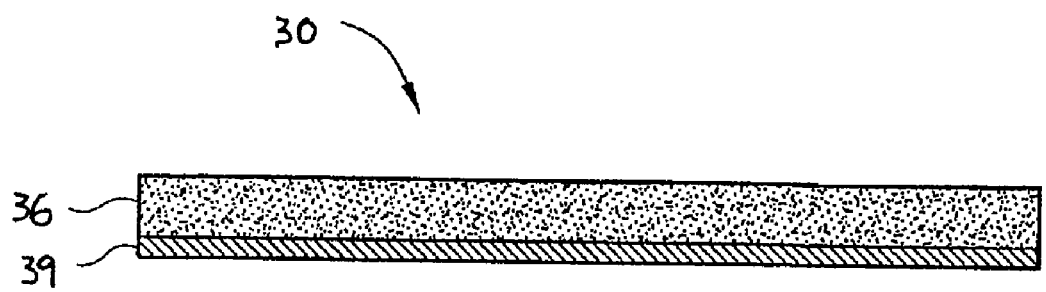
FIG. 3 is a schematic illustration of a medical device construct according to further aspect of the present invention.

FIG. 3 is a schematic illustration of an exemplary medical device construct 30, including an ECM material layer formed from a fluidized ECM solution, dried into a cake 36 and adhered to a biocompatible base substrate layer 39. In a preferred embodiment, the biocompatible base substrate layer 39 comprises a sheet containing at least one natural layer of extracellular matrix material.

Figure 4:
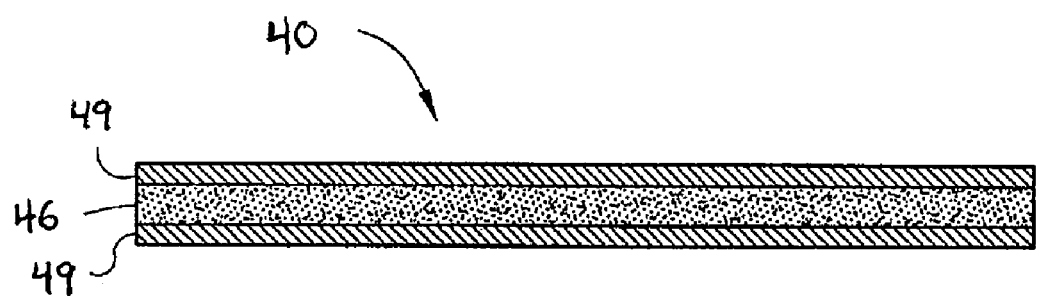
FIG. 4 is a schematic illustration of a medical device construct according to yet another aspect of the present invention.

FIG. 4 depicts an alternative medical device construct 40 in which a dried ECM-based cake layer 46 is sandwiched between two biocompatible base substrate layers 49. In a preferred embodiment, each biocompatible base substrate layer 49 comprises a sheet of extracellular matrix material.

The ECM-based cake layers can have any thickness desired. Generally, the thickness of this layer in certain embodiments will be from about 10 microns to about 10 mm, more typically about 0.1 mm to about 5 mm. A dried ECM-based cake layer will typically have a more open structure than the underlying base sheet material and will also in advantageous embodiments be less dense and/or less strong under tension than the underlying base or sheet material. Preferred dried cake layers will have a somewhat spongy character when dry.

The dried ECM-based cake may be subjected to further processing if desired, including for example cross-linking with any suitable agent such as radiation, chemical agents, or the like. In certain embodiments, treatment to cross-link the cake or layer is not performed (i.e. no additional cross-linking is introduced into the fibrillar mass), and in such embodiments desirable biotropic properties, including angiogenic properties, of the deposited layer can be retained. In other embodiments, cross-linking may be undertaken, but to an extent wherein the deposited cake retains bioactive (e.g. angiogenic) properties. These and other variations in processing of the deposited cake will occur to the skilled artisan in view of the teachings herein.

The drying of the deposited gel or other liquid-containing composition to form a dried cake or mass may be conducted in any suitable fashion. Preferably, the drying is conducted by a lyophilization technique, including for example a lyophilization technique involving freeze-drying and/or evaporative cooling. Other drying techniques such as air drying, drying under heated conditions, or vacuum pressing, may also be used to provide all or portion of the drying function.

In one aspect, a bioremodelable ECM material (sheet or fluidized) is adhered to a biocompatible base substrate in which the base substrate includes or is made from an ECM sheet material. An exemplary ECM sheet material is a sheet of submucosa tissue graft material (OASIS® Wound Matrix, Cook Biotech Incorporated, West Lafayette, Ind., USA).

When attached to a biocompatible substrate layer, the fluidized ECM material constitutes a biotropic mass of submucosa-derived components adhered to at least one substrate layer surface. A dried or gelled layer of fluidized ECM may be sandwiched or otherwise positioned between two substrate layers. Alternatively, one or more dried or gelled layers of fluidized ECM may be adhered to one or more base substrate layers.

A wide variety of biocompatible base substrate materials may be used. Exemplary base substrate materials include sheet or other substrate materials comprised of biopolymers such as collagen or gelatin, as well as sheet or other substrate materials made from synthetic polymers, resorbable and/or non-resorbable. Substrate materials made with combinations of biopolymers and synthetic polymers are also suitable for use in the invention. In a preferred embodiment, the substrate material is bioremodelable. An exemplary substrate material is a sheet of submucosa tissue graft material (OASIS® Wound Matrix, Cook Biotech Incorporated, West Lafayette, Ind., USA).

The biocompatible base substrate may be formed as a monolayer. Alternatively, a variety of techniques for laminating materials, including ECMs, together are known and may be used to prepare multilaminate base substrates. For example, a plurality of (i.e. two or more) layers of collagenous material, for example submucosa-containing or other ECM material, may be bonded together to form a multilaminate structure. Illustratively, two, three, four, five, six, seven, or eight or more collagenous layers containing submucosal or other collagenous ECM materials may be bonded together to provide a multilaminate collagenous substrate material for use in the present invention. In certain embodiments, two to six collagenous, submucosa-containing layers isolated from intestinal tissue of a warm-blooded vertebrate, particularly small intestinal tissue, are bonded together. Porcine-derived small intestinal tissue is preferred for this purpose. The layers of collagenous tissue may be bonded together in any suitable fashion, including dehydrothermal bonding under heated, non-heated or lyophilization conditions, using adhesives, glues or other bonding agents, crosslinking with chemical agents or radiation (including UV radiation), or any combination of these with each other or other suitable methods.

In one aspect, one or more layers of ECM sheet material (monolayer or multilaminate) containing bismuth thiols with or without other bioactive agents may be directly applied to the wound bed. Secondary dressing materials may be applied over the sheet of ECM material to keep the wound moist and to allow the flow and absorption of wound exudates. Suitable secondary dressing materials include Adaptic® Dressing (Ethicon Inc., Somerville, N.J., USA), DuoDERM CGF Control Gel Formula Dressings (ConvaTec, A Bristol Myers Suibb Company, Princeton, N.J., USA) and various others known to those of skill in the art.

Alternatively, the ECM materials may be adhesively secured to a wound area or other tissue defect by coating one or more skin or other tissue contacting surfaces of the medical device construct or medical product with a suitable adhesive. Suitable adhesives include pressure-sensitive adhesives. The adhesive may be attached to one or more release sheets to provide aseptic protection for the coated front surface of the wound-contacting surface of the dressing and to facilitate precise positioning of the dressing over the wound or other defect. Suitable adhesives and release (or attachment) sheets are described in U.S. Pat. No. 5,052,281, which is incorporated by reference herein.

In another aspect, an ECM gel layer may be disposed between a wound-contacting or defect-contacting film or sheet and an absorbent layer. Such a configuration may provide a more moist wound/defect environment for prolonged periods. Since fluidized gels are known to be useful in providing controlled release of bioactive agents, biofilm-inhibiting agents, wound healing agents and the like may be incorporated in the fluidized gel formulations for delivery to the wound bed.

In another aspect, a bioremodelable ECM gel layer is adhered to a top sheet film, which is formulated to allow fluid from the wound or defect to pass through the sheet toward the ECM gel layer, but to restrict the passage of liquid back towards the wound or defect. Preferably the wound/defect facing surface of the top sheet film is made hydrophobic so as to reduce adherency of the top sheet to the wound or other defect.

The wound or defect contacting sheet may include a top sheet film formed from a thermoplastic film-forming polymer. Preferably, the polymer is conformable but not substantially elastomeric. Exemplary polymers include, but are not limited to, polyethylene, polypropylene, polyester, polyamides such as nylons, fluoropolymers such as polyvinylidene fluoride (PVDF) or polytetrafluoroethylene (PTFE), and mixtures thereof. The top sheet is preferably a polyolefin film. Preferably, the film has a thickness by weight (ASTM E252-84) of from 10 to 200 micrometers, more preferably from 25 to 100 micrometers.

Additionally, the top sheet is preferably formed from a substantially liquid-impermeable sheet material provided with tapered capillaries, each capillary having a base substantially in the plane of the wound or defect facing surface of the top sheet and an apical opening remote from the wound or defect facing surface of the top sheet and preferably in contact with the gel and/or the absorbent layer. The conical capillaries provide rapid one-way wicking of fluid from the front of the top sheet, with minimal wet-back (i.e. back flow of fluid toward wound). Top sheets of the above type are described in GB-A-1526778 and US 2005/0256437.

In a further aspect, an ECM material (sheet or gel) is adhered to a second biocompatible base substrate in the form of an absorbent layer or wicking layer to absorb fluids and exudate from the wound or other defect. The absorbent or wicking layer may be formed from one or more layers or plies of the same or different absorbent materials. Preferably, the wicking layer is substantially the same size and shape as the wound/defect-facing layer, or slightly smaller than the wound/defect-facing layer.

The absorbent layer or wicking layer is preferably formed from any one of a variety of conventional materials for absorbing wound exudates, fluids, serum, or blood known in the wound healing art, including thermoplastic, water-swellable polymer films; absorbent foams; hydrogel materials; gauzes; nonwoven, woven, and knitted fabrics; superabsorbents; and mixtures thereof. The absorbent layer may be made from any of the absorbent materials described in U.S. Pat. Nos. 5,981,822 and 6,566,577, which are incorporated by reference herein.

The ECM material layer or the absorbent layer may be further adhered to a backing sheet layer formed from a breathable, substantially microbe-impermeable, liquid impermeable material or film configured to protect the wound or defect from further microbial infection or contamination and to prevent or reduce leakage of wound or defect exudate into clothes, bedclothes, etc. Suitable backing sheet layers and backing layer materials are described in U.S. Pat. No. 6,566,577, which is incorporated by reference herein.

Wound dressings or other medical products of the present invention may further comprise one or more protective cover sheets over any exposed surface or surface adhesive. For example, the protective cover sheets may include one or more release-coated paper cover sheets. Preferably, the wound dressing or other product is sterile and packaged in a microorganism-impermeable container.

Wound dressings or other products may be supplied in standard configurations suitable for application to a variety of wounds or defects and may be applied as is or may be cut, molded or otherwise shaped prior to application to a particular application site. Alternatively, the wound dressings or other medical products may be configured for a specific wound or specific wound or defect type. Wound dressings may be adapted for localized wound applications or as whole wound dressings. In certain embodiments, the medical product is sized, shaped and exhibits sufficient strength to treat a hernia. In other embodiments, the medical product is formed into a plug or other shape and used to treat a fistula.

A wound dressing or other medical product may be supplied and/or applied to a wound or defect as moist material ready for application to a wound or defect area or it may be supplied and/or applied as a dried material that can be rehydrated (with saline, for example) upon or prior to application to a wound or defect area. In some embodiments, a biological glue or tissue adhesive may be provided between a debrided wound bed surface and a contacting layer or sheet of ECM material to hold the ECM material in a stationary position against the wound bed surface.

An exemplary tissue adhesive is BioGlue® (CryoLife, Inc.). Other suitable adhesives include fibrin-, fibrinogen-, and thrombin-based sealants, bioactive ceramic-based sealants, and cyanoacrylate sealants, including, but not limited to, Vitex (V.I. Technologies, NY; comprising thrombin:fibrinogen in a 1:1 ratio); Quixil (Omrix Biopharm SA, Brussels); Dermabond, an octylcyanoacrylate tissue adhesive (Bruns and Worthington (2000) Am. Fam. Physician 61:1383-1388); Tisseel (Baxter International, Deerfield, Ill.); Hemaseel APR (Haemacure, Sarasota, Fla.); PlasmaSeal (Plasmaseal, San Francisco, Calif.); AutoSeal (Harvest Technologies, Norwell, Mass.); Floseal (Fusion Medical Technologies, Mountain View, Calif.); and Bioglass (U.S. Biomaterials, Alachua, Fla.); CoStasis (Cohesion Technologies). Med Pro Month (1999) 9:261-262; and MedPro Month (2000) 10:86-91.

The tissue adhesive may be bioresorbable. A bioresorbable adhesive may be formed by forming intermacromolecular complexes of a carboxypolysaccharide and, optionally, a polyether, such as polyethylene oxide. The carboxypolysaccharide may be of any biocompatible sort, including but not limited to carboxymethyl cellulose (CMC), carboxyethyl cellulose, chitin, hyaluronic acid, starch, glycogen, alginate, pectin, carboxymethyl dextran, carboxymethyl chitosan, and glycosaminoglycans such as heparin, heparin sulfate, and chondroitin sulfate. It is within the scope of this disclosure, however, to include any type of tissue adhesive sufficient for adhering ECM materials to the wound bed surface.

The wound dressings disclosed herein may be used to create bioresorbable wound dressings or band-aids. Wound dressings may be used as a wound-healing dressing, a tissue sealant (i.e., sealing a tissue or organ to prevent exposure to a fluid or gas, such as blood, urine, air, etc., from or into a tissue or organ), and/or a cell-growth scaffold. In various embodiments, the wound dressing may protect the injured tissue, maintain a moist environment, be water permeable, be easy to apply, not require frequent changes, be non-toxic, be non-antigenic, maintain microbial control, and/or may deliver effective healing agents to the wound site.

Examples of bioresorbable sealants and adhesives that may be used in accordance with the wound dressing described herein include, for example, FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CyoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geek; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND™ which consists of 2-Octyl Cyanoacrylate produced by Dermabond (Ethicon); TISSUEGLU® produced by Medi-West Pharma; and VETBOND™ which consists of n-butyl cyanoacrylate produced by 3M.

Natural, Bioremodelable ECM Source Materials

In accordance with the present invention, the wound dressing includes a carrier. In one aspect, the carrier is formed from natural, bioremodelable materials. In a preferred embodiment, the carrier is formed from extracellular matrix (ECM) material(s), which are preferably bioremodelable. Upon application of the wound dressing to the body of a subject, the bioremodelable material in the wound dressing may serve as a matrix to promote and/or induce the growth and/or bioremodeling of endogenous tissue. These are properties particularly suited to meet the requirements for healing wounds and other tissue defects. Bioremodelable materials of the present invention are preferentially selected to facilitate the process of bioremodeling, which may include: (1) stimulation in the infiltration of native cells into an acellular matrix; (2) stimulation of new blood vessel formation (capillaries) growing into the matrix to nourish the infiltrating cells (angiogenesis); and/or (3) effecting the degradation and/or replacement of the bioremodelable material by endogenous tissue upon implantation into a host.

Bioremodelable materials have been used successfully in vascular grafts, urinary bladder and hernia repair, replacement and repair of tendons and ligaments, and dermal grafts. When used in such applications, the graft constructs appear not only to serve as a matrix for the regrowth of the tissues replaced by the graft constructs, but also to promote or induce such regrowth of endogenous tissue. Common events in the remodeling process include widespread, rapid neovascularization, proliferation of granulation mesenchymal cells, biodegradation/resorption of implanted intestinal submucosal tissue material, and lack of immune rejection. When positioned in a wound area, the wound dressing is capable of being ultimately replaced by endogenous host tissues.

Bioremodelable ECM materials for use in the present invention may possess one or more angiogenic properties. Angiogenesis represents a crucial step in tissue formation in response to biomaterial implantation, especially necessary for implants that are designed to foster tissue growth. Angiogenesis is a complex process that depends on many mechanisms occurring in an organized manner (P. Carmeliet, Mechanisms of angiogenesis and arteriogenesis, Nat Med 6 (2000), no. 4, 389-395). Due to the complexity necessary for proper angiogenesis, biomaterial interaction with the host environment can have a dramatic effect on the quality and quantity of the angiogenic activity. Methods for measuring in vivo angiogenesis in response to biomaterial implantation have recently been developed. One such method uses a mouse subcutaneous implant model to determine the angiogenic potential (Heeschen, C. et al., Nat Med vol. 7, no. 7, pp. 833-839, 2001). When combined with a fluorescence microangiography technique (Johnson, C. et al., Circ Res., vol. 94, no. 2, pp. 262-268, 2004), this model can give quantitative and qualitative measures of angiogenesis into biomaterials.

Bioremodelable materials may include naturally-derived collagenous ECM materials isolated from suitable animal or human tissue sources. As used herein, it is within the definition of a "naturally-derived ECM" to clean, delaminate, and/or comminute the ECM, or to cross-link the collagen or other components within the ECM. It is also within the definition of naturally occurring ECM to fully or partially remove one or more components or subcomponents of the naturally occurring matrix.

Bioremodelable ECM materials possess biotropic properties capable of inducing tissue remodeling. Suitable ECM materials which can be processed to provide bioremodelable materials include, for example, submucosal (including for example small intestinal submucosa (SIS), stomach submucosa, urinary bladder submucosa, or uterine submucosa, each of these isolated from juvenile or adult animals), renal capsule membrane, dermal collagen, amnion, dura mater, pericardium, serosa, peritoneum or basement membrane layers or materials, including liver basement membrane or epithelial basement membrane materials.

Submucosal tissue materials may be isolated and used as intact natural sheet forms, as reconstituted collagen layers including collagen derived from these materials, or as fluidized submucosal solutions configured in the form of a gel, foam or a sponge. For additional information as to submucosa materials useful in the present invention, and their isolation and treatment, reference can be made to U.S. Pat. Nos. 4,902,508, 5,554,389, 5,733,337, 5,993,844, 6,206,931, 6,099,567, and 6,331,319. Renal capsule membrane can also be obtained from warm-blooded vertebrates, as described more particularly in International Patent Application serial No. PCT/US02/20499, published as WO 03002165. Commercially available ECM materials capable of remodeling to the qualities of its host when implanted in human soft tissues include porcine SIS material (Surgisis® line of SIS materials, Cook Biotech Inc., West Lafayette, Ind.) and bovine pericardium (Peri-Strips®, Synovis Surgical Innovations, St. Paul, Minn.).

The following U.S. patents, hereby incorporated by reference, disclose the use of ECMs for the regeneration and/or repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,762,966; 5,755,791; 5,753,267; 5,733,337; 5,711,969; 5,645,860; 5,641,518; 5,554,389; 5,516,533; 5,460,962; 5,445,833; 5,372,821; 5,352,463; 5,281,422; and 5,275,826.

Preferred ECM materials contain residual bioactive proteins or other ECM components derived from the tissue source of the materials. For example, they may contain fibroblast growth factor 2 (basic FGF), vascular endothelial growth factor (VEGF), transforming growth factor-beta (TFG-beta), epidermal growth factor (EGF), platelet-derived growth factor (PDGF), and/or isoforms or combinations thereof. It is also expected that ECM base materials of the invention may contain additional residual bioactive agents including, for example, one or more of glycosaminoglycans, glycoproteins, proteoglycans, and/or growth factors.

Further, in addition or as an alternative to the inclusion of native bioactive agents, non-native bioactive agents such as those synthetically produced by recombinant technology or other methods, may be incorporated into the ECM materials of the present invention. These non-native bioactive agents may be naturally-derived or recombinantly produced proteins that correspond to those natively occurring in the ECM tissue, but perhaps of a different species (e.g. human proteins applied to collagenous ECMs from other animals, such as pigs). The non-native bioactive substances may be applied to the ECM material during its preparation, prior to wound dressing application or it may be applied during or after engraftment of the ECM material in the patient. Exemplary non-native bioactive agents include growth factors, cytokines, protease inhibitors, and the like.

Other non-native bioactive agents that may be incorporated into the ECM materials or used in conjunction with the wound dressings of the present invention include any of the above described biofilm-inhibiting agents or bioactive agents, which are not ordinarily present in ECM materials, including but not limited to and analgesic agents, and the like.

Submucosal materials, including SIS materials, represent preferred examples of ECM materials for use with the present invention. The ECM materials may include residual bioactive proteins or other ECM components derived from the tissue source of the materials. The ECM materials may include (among others) fibroblast growth factor 2 (FGF-2), vascular endothelial growth factor (VEGF), transforming growth factor-beta (TGF-beta). It is also expected that ECM base materials of the invention may contain additional bioactive agents including, for example, one or more highly conserved collagens, growth factors, glycoproteins, proteoglycans, glycosaminoglycans, other growth factors, and other biological materials such as heparin, heparin sulfate, hyaluronic acid, fibronectin and the like. Thus, generally speaking, submucosal or other ECM materials may include a bioactive agent capable of inducing, directly or indirectly, a bioremodeling response reflected in a change in cell morphology, proliferation, growth, protein expression and/or gene expression. The bioactive agents in the ECM materials may be contained in their natural configuration and natural concentration.

ECM or submucosal materials may be isolated from warm-blooded vertebrate tissues including the alimentary, respiratory, intestinal, urinary or genital tracts of warm-blooded vertebrates. Preferred submucosal tissues may include intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine.

An exemplary submucosa material is small intestine submucosa (SIS). SIS has been shown to be acellular, strong, and exhibit a sidedness in that it has a differential porosity of its mucosal and serosal sides. Highly purified SIS generally does not trigger any negative immune system responses, generally is free of viral activity, and is known to reduce seepage. A preferred intestinal submucosal tissue source in accordance with the present invention is porcine SIS.

The preparation of intestinal submucosa is described in U.S. Pat. Nos. 6,206,931 and 6,358,284, the disclosures of which are incorporated by reference in their entirety herein. Urinary bladder submucosa and its preparation are described in U.S. Pat. No. 5,554,389, the disclosure of which is incorporated by reference in its entirety herein. Stomach submucosa and its preparation are described in U.S. Pat. No. 6,099,567, the disclosure of which is incorporated by reference in its entirety herein.

Preferred SIS material typically includes the tunica submucosa delaminated from both the tunica muscularis and at least the luminal portions of the tunica mucosa. The submucosal tissue may include the tunica submucosa and basilar portions of the tunica mucosa including the lamina muscularis mucosa and the stratum compactum. The preparation of intestinal submucosa is described in U.S. Pat. No. 4,902,508, and the preparation of tela submucosa are described in U.S. Pat. Nos. 6,206,931 and 6,358,284, all of which are incorporated by reference herein. The preparation of submucosa is also described in U.S. Pat. No. 5,733,337, Nature Biotechnology, vol. 17, p. 1083 (November 1999), and WO 98/22158. Also, a method for obtaining a highly pure, delaminated submucosa collagen matrix in a substantially sterile state was previously described in U.S. Pat. Pub. No. 2004/180042, which is incorporated by reference herein.

One preferred purification process involves disinfecting the submucosal tissue source, followed by removal of a purified matrix including the submucosa. It is thought that delaminating the disinfected submucosal tissue from the tunica muscularis and the tunica mucosa minimizes exposure of the submucosa to bacteria and other contaminants following delamination and better preserves the aseptic state and inherent biochemical form of the submucosa, thereby potentiating its beneficial effects. Alternatively, the ECM- or submucosa may be purified a process in which the sterilization step is carried out after delamination as described in U.S. Pat. Nos. 5,993,844 and 6,572,650. Still further preferred processes for preparing an SIS or other ECM so as to provide enhanced component profiles are described in U.S. Patent Application Ser. No. 60/853,584 filed Oct. 23, 2006 and International Application No. PCT/US2007/82238 filed Oct. 23, 2007, each of which is hereby incorporated by reference in its entirety. Accordingly, in certain embodiments, the ECM material retains collagen and non-collagen components, and desirably exhibits an angiogenic character. At the same time, the submucosa-containing or other ECM material has low levels of undesired components such as native lipids, nucleic acids (e.g. DNA), and/or immunoglobulin A (IgA) components. In some embodiments, the ECM can be a sterile, decellularized extracellular matrix (ECM) material including native fibroblast growth factor-2 (FGF-2), and native immunoglobulin A (IgA) at a level of no greater than 20 μg/g. In some forms, this ECM material can have a lipid content of no greater than about 4%. In still further aspects, the ECM material can have a native FGF-2 content of at least about 10 ng/g and at least one of, and in certain forms each of (i) native IgA at a level of no greater than about 20 μg/g; (ii) native lipids at a level of no greater than about 4% by weight; (iii); (iv) native hyaluronic acid at a level of at least about 50 μg/g; and (v) native sulfated glycosaminoglycan at a level of at least about 500 μg/g. These unique ECM materials can be prepared by processing methods that comprise treating a relatively impure ECM starting material to decrease the content of the undesired components, such as nucleic acid, lipids and/or immunoglobulins such as IgA, while retaining substantial levels of desired components such as growth factor(s), proteoglycans and/or glycosaminoglycans (GAGs). Typically, to prepare such preferred ECM materials, an ECM starting material will be treated with a mild detergent solution, such as an ionic or nonionic detergent solution. The low concentration of detergent enables a retention of a substantial level of desired components, such as those as noted above. In certain modes of operation, the ECM material will be treated with an aqueous solution of sodium dodecyl sulfate (SDS) or another ionic or nonionic detergent at a detergent concentration of about 0.05% to about 1%, more preferably about 0.05% to about 0.3%. This treatment can be for a period of time effective to disrupt cell and nuclear membranes and to reduce the immunoglobulin (e.g. IgA) content of the ECM material, typically in the range of about 0.1 hour to about 10 hours, more typically in the range of about 0.5 hours to about 2 hours. Processing the isolated ECM material in this manner preferably disrupts cell and nuclear membranes and results in a material with a substantially reduced its IgA content, thus reducing the immunogenicity of the material. In addition to treating an ECM material with a detergent medium, the ECM material can be contacted with other agents that participate in achieving the desired ECM component profile. For example, the ECM material can be treated with an aqueous medium, preferably basic, in which DNA is soluble. Such a medium can in certain forms have a pH in the range of above 7 to about 9, with pH's in the range of about 8 to about 8.5 proving particularly beneficial in some embodiments. The basic aqueous medium can include a buffer, desirably a biocompatible buffer such as tris(hydroxymethyl)aminomethane (TRIS), and/or a chelating agent such as ethylene diamine tetraacetic acid (EDTA). In one preferred form, the nucleic acid solubilizing medium is a TRIS-borate-EDTA (TBE) buffer solution. This treatment with a DNA solubilizing medium can be for a period of time effective to reduce the DNA content of the ECM material, typically in the range of about 0.1 hour to about 10 hours, more typically in the range of about 0.5 hours to about 2 hours. In addition to treatment with detergent and DNA-solubilization media, methods of preparing medical graft materials of the invention can involve treatment with a liquid medium that results in a substantial reduction of the level of lipid components of the ECM material. For example, the resulting native lipid content of the ECM material can be reduced to no greater than about 4% in certain embodiments. This can be accomplished, for example, by a preparative process that involves a step of treating the ECM material with a liquid organic solvent in which the lipids are soluble. Suitable such organic solvents include for example water-miscible solvents, including polar organic solvents. These include low molecular weight (e.g. $C_1$ to $C_4$) alcohols, e.g. methanol, ethanol, isopropanol, and butanols, acetone, chloroform, and others. This treatment with a lipid-removing medium can be for a period of time effective to reduce the lipid content of the ECM material, typically in the range of about 0.1 hour to about 10 hours, more typically in the range of about 0.1 hours to about 1 hours. In certain embodiments, multiple (two or more) such treatments will be conducted.

The stripping of the submucosal tissue source is preferably carried out by utilizing a disinfected or sterile casing machine, to produce submucosa, which is substantially sterile and which has been minimally processed. A suitable casing machine is the Model 3-U-400 Stridhs Universal Machine for Hog Casing, commercially available from the AB Stridhs Maskiner, Gotoborg, Sweden. As a result of this process, the measured bioburden levels may be minimal or substantially zero. Other means for delaminating the submucosa source can be employed, including, for example, delaminating by hand.

In this method, a segment of vertebrate intestine, preferably harvested from porcine, ovine or bovine species, may first be subjected to gentle abrasion using a longitudinal wiping motion to remove both the outer layers, identified as the tunica serosa and the tunica muscularis, and the innermost layer, i.e., the luminal portions of the tunica mucosa. The submucosal tissue is rinsed with water or saline, optionally sterilized, and can be stored in a hydrated or dehydrated state. Delamination of the tunica submucosa from both the tunica muscularis and at least the luminal portions of the tunica mucosa and rinsing of the submucosa provide an acellular matrix designated as submucosal tissue. The use and manipulation of such material for the formation of ligament and tendon grafts and the use more generally of such submucosal tissue constructs for inducing growth of endogenous connective tissues is described and claimed in U.S. Pat. No. 5,281,422, disclosure of which is incorporated herein by reference.

Following delamination, submucosa may be sterilized using any conventional sterilization technique including glutaraldehyde, formaldehyde, acidic pH, propylene oxide, ethylene oxide, gas plasma sterilization, electron beam (E-beam) or other radiation sterilization or peracetic acid sterilization, or combinations thereof, and the like. Sterilization techniques which do not adversely affect the mechanical strength, structure, and biotropic properties of the purified submucosa are preferred. Certain preferred sterilization techniques also include exposing the graft to ethylene oxide treatment or gas plasma sterilization. Typically, the purified submucosa is subjected to two or more sterilization processes. After the purified submucosa is sterilized, for example by chemical treatment, the matrix structure may be wrapped in a plastic or foil wrap and sterilized again using electron beam or gamma irradiation sterilization techniques. Certain sterilization techniques may be found to be more compatible with a particular bismuth thiol coated medical product. It will be understood that in such instances, the sterilization technique(s) that are found to be most compatible can be used.

Preferred submucosa may be characterized by the low contaminant levels set forth in Table 1 below. The contaminant levels in Table 1 may be found individually or in any combination in a given ECM sample. The abbreviations in Table 1 are as follows: CFU/g=colony forming units per gram; PFU/g=plaque forming units per gram; µg/mg=micrograms per milligram; ppm/kg=parts per million per kilogram.

TABLE 1

|  | First Preferred Level | Second Preferred Level | Third Preferred Level |
|---|---|---|---|
| ENDOTOXIN | <12 EU/g | <10 EU/g | <5 EU/g |
| BIOBURDEN | <2 CFU/g | <1 CFU/g | <0.5 CFU/g |
| FUNGUS | <2 CFU/g | <1 CFU/g | <0.5 CFU/g |
| NUCLEIC ACID | <10 µg/mg | <5 µg/mg | <2 µg/mg |
| VIRUS | <500 PFU/g | <50 PFU/g | <5 PFU/g |
| PROCESSING AGENT | <100,000 ppm/kg | <1,000 ppm/kg | <100 ppm/kg |

The ECM portion of the wound dressing or other medical product may be provided as a single, hydrated sheet of ECM tissue material, such as SIS. A sheet of ECM material may be formed from one or multiple sheets of ECM material. In multilayered ECM embodiments, the individual sheets may be positioned in any number of orientations relative to each other. It is further within the scope of the disclosure for the ECM layer(s) to have any reasonable thickness for use in the dressing or product. A sheet of ECM material may be sized to fit the wound or other defect and to be sufficiently flexible to conform to any complex wound/defect or wound/defect surface. Additionally, the ECM materials may be provided in fresh, frozen, or lyophilized (freeze-dried) forms. Lyophilization of the ECM material may provide increased porosity and enhanced tissue ingrowth capacity to an ECM sheet. Lyophilized ECM materials may be used in the dried form, or they may be hydrated prior to use.

ECM sheet materials applied to a wound or other tissue defect surface may be fenestrated (or perforated) or meshed (or slitted) to prevent fluid accumulation below the SIS layer. Any conventional mechanical means for perforating or fenestrating skin grafts may be used to fenestrate ECM materials of the present invention. The fenestrations, or perforations, in the ECM sheet materials may permit blood and cells from the wound or defect to migrate into the ECM material layer(s) to start the tissue growth in the ECM framework of the sheet material. The fenestrations may further allow exudate materials to flow upward and become absorbed by biocompatible substrate materials overlaying the ECM materials. This can serve to maintain the ECM material(s) in direct contact with the wound or defect bed, rather than floating off the bed.

Meshed ECM sheet materials are generally characterized by multiple generally parallel rows of slits, whereby the termini of the slits in adjacent rows are longitudinally offset from one another. Compositions and methods for making meshed ECM sheet materials are described in U.S. Patent Application Publication No. US 2005/0021141, the disclosures of which are expressly incorporated by reference herein.

Additionally, ECM portions of the disclosed wound dressing or other product may be optimally configured by stretching or by laminating together multiple pieces, layers or strips of submucosal or other ECM tissue compressed under e.g., dehydrating conditions in accordance with the teachings set forth in U.S. Pat. Nos. 6,206,931 and 6,358,284, which are incorporated by reference herein. The laminated submucosal (e.g. SIS) or other ECM assembly optionally further physically crosslinked by partially or fully drying (down to less than 15% moisture content) under vacuum pressure. Alternatively, the laminated SIS or other ECM assembly is lyophilized, instead of being vacuum dried, to increase its porosity.

SIS in its normal sheet form has widely varying differences in its thickness and porosity on any given piece of material. Instead of using the SIS or other ECM material in its normally occurring sheet form, the SIS or ECM may be cut into pieces or can be shredded or ground into small sized bits or particles. These small pieces or bits may then be uniformly sprayed, formed, coated or cast on any part or substrate of the wound dressing. Malleable, hydrated pieces of ECM material may be cast on or applied like papier mache to a form. After the cast is dried or allowed to harden, the form can be removed. The SIS or ECM particles can be sprayed, coated or cast onto one or more components of the wound dressing or mandrel with or without a binder material to enhance the physical strength of the resulting structure.

ECM materials may be stored in a hydrated or dehydrated state. Lyophilized or air dried submucosal or other ECM materials may be rehydrated and used in accordance with this invention without significant loss of its biotropic, thromboresistant or mechanical properties.

ECM Gel Materials

ECM or submucosal tissue of the present invention may be further processed into sheet form, chunks, or alternatively, in fluidized or powdered forms. SIS material may be in a form of a sponge-like or foam-like SIS (lyophilized SIS sponge, such as SURGISIS™ Soft-Tissue Graft (SIS) [Cook Biotech, Inc., West Lafayette, Ind.]) capable of greatly expanding in diameter as it absorbs therapeutic material, or non-sponge material including a sheet of SIS. Fluidized or powdered forms of submucosa may be prepared using the techniques described in U.S. Pat. Nos. 5,275,826 and 6,206,931, and U.S. Pat. Appl. Publ. No. 20060201996, the disclosures of which are expressly incorporated herein by reference in their entirety. These forms can also be applied to other ECM materials.

Fluidized ECM materials can be advantageously applied to the wound dressings or other products of the present invention for delivering biofilm inhibiting and/or wound- or defect-healing promoting agents. In one aspect, bismuth thiols and/or other biofilm-inhibiting agents are mixed with fluidized ECM material to form a substantially homogenous biofilm-inhibiting solution. The fluidized ECM material may be dried or formed into a gel for direct use.

For example, comminuted submucosal or other ECM material can be dried by freeze drying to form a powder, which can hydrated, that is, combined with water or buffered saline and optionally other pharmaceutically acceptable excipients, to form a fluid ECM tissue composition. The viscosity of fluidized ECM compositions may be manipulated by controlling the concentration of the submucosa or other ECM component, the degree of hydration and adjusting the pH of the submucosal or other ECM digest. The viscosity may be adjusted to a range of about 2 to about 300,000 cps at 25° C. Higher viscosity gel formulations can have a gel or paste consistency and may be prepared by adjusting the pH of the digest solutions to about 6.0 to about 7.0.

Alternatively, the fluidized ECM material may be dried and adhered to one or more biocompatible base substrates. The resulting construct includes an adherent biotropic fibrous mass of submucosa- or other ECM-derived components formed on at least one substrate surface. A dried or gelled layer of fluidized ECM may be sandwiched or otherwise positioned between two substrate layers. Alternatively, one or more dried or gelled layers of fluidized ECM may be adhered to one or more base substrate layers. Preferably the biocompatible base substrate includes or is made from ECM materials. Any construct or wound dressing containing a layer of fluidized ECM may be dried by lyophilization.

In a particular aspect, a submucosal or other ECM gel composition is applied to a sheet of submucosa tissue graft material (e.g., OASIS® Wound Matrix, Cook Biotech Incorporated, West Lafayette, Ind., USA). The gel composition may be prepared as in described in U.S. Pat. No. 5,275,826, which is incorporated by reference in its entirety herein. The gel composition may be applied to a submucosa or other ECM tissue graft sheet material to provide a layer thickness of about 1 to 2 mm. After the gel composition is allowed to gel, the resulting construct may be dried by lyophilization.

The formation of the fluidized ECM components can be achieved in any suitable manner. Any suitable source of bioremodelable ECM material can be used to prepare a solubilized mixture including components of the material. The liquid or flowable composition including solubilized extracellular matrix components may be generally prepared at follows. Briefly, the ECM material is digested in an acidic or basic medium by contact with an appropriate enzyme or combination of enzymes. To aid in this digestion, the ECM material may be first reduced to a particulate form by tearing, cutting, grinding or shearing the isolated ECM material. Illustratively, shearing may be conducted in a fluid medium, and grinding may be conducted with the material in a frozen state. For example, the material can be contacted with liquid nitrogen to freeze it for purposes of facilitating grinding into powder form. Such techniques can involve freezing and pulverizing submucosa under liquid nitrogen in an industrial blender.

Next, the particulate ECM material may be subjected to digestion using any suitable enzyme in an enzymatic digestion step. Such enzymes include for example serine proteases, aspartyl proteases, and matrix metalloproteases. The concentration of the enzyme may be adjusted based on the specific enzyme used, the amount of ECM to be digested, the duration of the digestion, the temperature of the reaction, and the desired properties of the bioremodelable fibril mass layer forming material. In an illustrative embodiment, about 0.1% to about 0.2% of enzyme (pepsin, for example) may be used and the digestion may be conducted under cooled conditions for a period of time sufficient to substantially digest the ECM material. The digestion may be conducted at any suitable temperature, preferably at temperatures between about 4° C. and about 37° C. Likewise, any suitable duration of digestion may be used, such durations typically falling in the range of about 2 to 180 hours. The ratio of the concentration of ECM material (hydrated) to total enzyme usually ranges from about 25 to about 125 and more typically the ratio is about 50, and the digestion is conducted at approximately 4° C. for approximately 24-72 hours. When an enzyme is used to aid in the digestion, the digestion will be performed at a pH at which the enzyme is active and more advantageously at a pH at which the enzyme is optimally active. Illustratively, pepsin exhibits optimal activity at pH's in the range of about 2 to 4.

If necessary or desired, the enzymes or other disruptive agents used to solubilize the ECM material may be removed or inactivated before proceeding with the formation of the mass layer. Also, any disruptive agent, particularly enzymes, that remains present and active during storage of the tissue may potentially change the composition and potentially the layer forming characteristics of the solution. Enzymes, such as pepsin, may be inactivated with protease inhibitors, a shift to neutral pH, a drop in temperature below 0° C., heat inactivation, or through the removal of the enzyme by fractionation. A combination of these methods may be utilized to stop digestion of the ECM material at a predetermined endpoint, for example the ECM material may be immediately frozen and later fractionated to limit digestion.

Illustratively, during preparation of a suitable fibrous mass layer forming material, the ECM material may be enzymatically digested for a sufficient time to produce a hydrolysate of ECM components. Accordingly, the ECM may be treated with one enzyme or with a mixture of enzymes to hydrolyze the structural components of the material and prepare a hydrolysate having multiple hydrolyzed components of reduced molecular weight. The length of digestion time may be varied depending on the application, and the digestion may be extended to completely solubilize the ECM material. In some modes of operation, the ECM material will be treated sufficiently to partially solubilize the material to produce a digest composition comprising hydrolyzed ECM components and nonhydrolyzed ECM components. The digest composition may then, in illustrative embodiments, be further processed to remove at least some of the nonhydrolyzed components. For example, the nonhydrolyzed components may be separated from the hydrolyzed portions by centrifugation, filtration, or other separation techniques known in the art.

Illustratively, preferred gel-form fibrous mass layer forming materials may be prepared from enzymatically digested vertebrate ECM material that has been fractionated under acidic conditions, for example including pH ranging from about 2 to less than 7, especially to remove low molecular weight components. Typically, the ECM hydrolysate is fractionated by dialysis against a solution or other aqueous medium having an acidic pH, e.g. a pH ranging from about 2 to about 7. In addition to fractionating the hydrolysate under acidic conditions, the ECM hydrolysate is typically fractionated under conditions of low ionic strength with minimal concentrations of salts such as those usually found in standard buffers such as PBS (i.e. NaCl, KCl, $Na_2HPO_4$, or $KH_2PO_4$) that can pass through the dialysis membrane and into the hydrolysate. Such fractionation conditions work to reduce the ionic strength of the ECM hydrolysate and thereby provide enhanced gel forming characteristics.

The hydrolysate solution produced by enzymatic digestion of the ECM material has a characteristic ratio of protein to carbohydrate. The ratio of protein to carbohydrate in the hydrolysate is determined by the enzyme utilized in the digestion step and by the duration of the digestion. The ratio may be similar to or may be substantially different from the protein to carbohydrate ratio of the undigested ECM tissue. For example, digestion of vertebrate ECM material with a protease such as pepsin, followed by dialysis, will form a fractionated ECM hydrolysate having a lower protein to carbohydrate ratio relative to the original ECM material.

Flowable ECM compositions capable of forming shape retaining gels may be used as fibrous mass layer forming material in the present invention. Such ECM compositions can be prepared from ECM material that has been enzymatically digested and fractionated under acidic conditions to form an ECM hydrolysate that has a protein to carbohydrate ratio different than that of the original ECM material. Such fractionation can be achieved entirely or at least in part by dialysis. The molecular weight cut off of the ECM components to be included in the gellable material is selected based on the desired properties of the gel. Typically the molecular weight cutoff of the dialysis membrane (the molecular weight above which the membrane will prevent passage of molecules) is within in the range of about 2000 to about 10000 Dalton, and more preferably from about 3500 to about 5000 Dalton.

In certain forms of the ECM mass layer forming material composition, apart from the potential removal of undigested ECM components after the digestion step and any controlled fractionation to remove low molecular weight components as discussed above, the ECM hydrolysate is processed so as to avoid any substantial further physical separation of the ECM components. For example, when a more concentrated ECM hydrolysate material is desired, this may be accomplished by removing water from the system (e.g. by evaporation or lyophilization) as opposed to using conventional "salting out"/centrifugation techniques that would demonstrate significant selectivity in precipitating and isolating collagen, leaving behind amounts of other desired ECM components. Thus, in certain embodiments of the invention, solubilized ECM components of the ECM hydrolysate remain substantially unfractionated, or remain substantially unfractionated above a predetermined molecular weight cutoff such as that used in the dialysis membrane, e.g. above a given value in the range of about 2000 to 10000 Dalton, more preferably about 3500 to about 5000 Dalton.

In the manufacture of the flowable ECM material, vertebrate ECM material may be stored frozen (e.g. at about −20 to about −80° C.) in either its solid, comminuted or enzymatically digested forms, or the material may be stored after being hydrolyzed and fractionated. The ECM material may be stored in solvents that maintain the collagen in its native form and solubility. For example, one suitable storage solvent is 0.01 M acetic acid, however other acids may be substituted, such as 0.01 N HCl. In one form, the fractionated ECM hydrolysate may be dried (by lyophilization, for example) and stored in a dehydrated/lyophilized state. The dried form may be rehydrated to prepare a flowable ECM composition capable of forming a gel that may be used as a fibril mass layer forming material in the present invention.

In accordance with an illustrative method of fibril mass layer forming material preparation, the fractionated ECM hydrolysate or other flowable ECM composition will exhibit the capacity to gel upon adjusting the pH of a relatively more acidic aqueous medium containing it to about 5 to about 9, more preferably about 6.6 to about 8.0, and typically about 7.2 to about 7.8, thus inducing fibrillogenesis and matrix gel assembly. In one embodiment, the pH of the fractionated hydrolysate may be adjusted by the addition of a buffer that does not leave a toxic residue, and has a physiological ion concentration and the capacity to hold physiological pH. Examples of suitable buffers include PBS, HEPES, and DMEM. Illustratively, the pH of the fractionated ECM hydrolysate may be raised by the addition of a buffered NaOH solution to 6.6 to 8.0, more preferably 7.2 to 7.8, to facilitate the formation of an ECM-containing gel. Any suitable concentration of NaOH solution may be used for these purposes, for example including about 0.05 M to about 0.5 M NaOH. In accordance with an embodiment, the ECM hydrolysate is mixed with a buffer and sufficient 0.25 N NaOH is added to the mixture to achieve the desired pH.

The ionic strength of the ECM hydrolysate is believed to be important in maintaining the fibers of collagen in a state that allows for fibrillogenesis and matrix gel assembly upon neutralization of the hydrolysate. Accordingly, if needed, the salt concentration of the ECM hydrolysate material may be reduced prior to neutralization of the hydrolysate. The neutralized hydrolysate may be caused to gel at any suitable temperature, e.g. ranging from about 4° C. to about 40° C. The temperature will typically affect the gelling times, which may range from about 5 to about 120 minutes at the higher gellation temperatures and about 1 to about 8 hours at the lower gellation temperatures. Typically, the hydrolysate will be effective to self-gel at elevated temperatures, for example at about 37° C. In this regard, preferred neutralized ECM hydrolysates will be effective to gel in less than about ninety minutes at 37° C., for example within about 30 seconds to thirty minutes at 37° C.

In alternative embodiments, additional components may be added to the ECM hydrolysate composition before, during, or after forming the fibrous mass layer. For example, one or more of the above described biofilm-inhibiting agents, wound healing agents or analgesics may be added. In certain embodiments, such materials are added prior to formation of the fibril mass layer. This may be accomplished for example by forming a dry mixture of a powdered ECM hydrolysate with the additional component(s), and then reconstituting and gelling the mixture, or by incorporating the additional component(s) into an aqueous, ungelled composition of the ECM hydrolysate before, during (e.g. with) or after addition of the neutralization agent. The additional component(s) may also be added to a formed ECM gel, e.g. by infusing or mixing the component(s) into the gel and/or coating them onto the gel. In certain embodiments, the gel may then be dried (e.g. by lyophilization).

In one illustrative fibrous mass layer forming material preparation, a particulate ECM material may be added to an ECM hydrolysate composition, which may then be incorporated in a formed gel and ultimately in a dried mass. Such particulate ECM materials may be prepared by cutting, tearing, grinding or otherwise comminuting an ECM starting material. For example, a particulate ECM material having an average particle size of about 50 microns to about 500 microns may be included in the gellable ECM hydrolysate, more preferably about 100 microns to about 400 microns. The ECM particulate may be added in any suitable amount relative to the hydrolysate, with preferred ECM particulate to ECM hydrolysate weight ratios (based on dry solids) being about 0.1:1 to about 200:1, more preferably in the range of about 1:1 to about 100:1. The inclusion of such ECM particulates in the ultimate gel or fibril mass layer forming material may serve to provide additional material that may function to provide bioactivity to the gel (e.g. itself including FGF-2 and/or other growth factors or bioactive substances as discussed herein) and/or serve as scaffolding material for tissue ingrowth.

In certain embodiments, flowable ECM compositions to be used as fibrous mass layer forming material in the invention may be disinfected by contacting an aqueous medium including ECM hydrolysate components with an oxidizing disinfectant. This mode of disinfection provides an improved ability to recover a disinfected ECM hydrolysate that exhibits the capacity to form beneficial gels. In certain preparative methods, an aqueous medium containing ECM hydrolysate components may be disinfected by providing a peroxy disinfectant in the aqueous medium. This can be advantageously achieved using dialysis to deliver the peroxy disinfectant into and/or to remove the peroxy disinfectant from the aqueous medium containing the hydrolysate. In certain disinfection techniques, an aqueous medium containing the ECM hydrolysate is dialyzed against an aqueous medium containing the peroxy disinfectant to deliver the disinfectant into contact with the ECM hydrolysate, and then is dialyzed against an appropriate aqueous medium (e.g. an acidic aqueous medium) to at least substantially remove the peroxy disinfectant from the ECM hydrolysate. During this dialysis step, the peroxy compound passes through the dialysis membrane and into the ECM hydrolysate, and contacts ECM components for a sufficient period of time to disinfect the ECM components of the hydrolysate. In this regard, typical contact times will range from about 0.5 hours to about 8 hours and more typically from about 1 hour to about 4 hours. The period of contact will be sufficient to substantially disinfect the digest, including the removal of endotoxins and inactivation of virus material present. The removal of the peroxy disinfectant by dialysis may likewise be conducted over any suitable period of time, for example over a duration of about 4 to about 180 hours, more typically of about 24 to about 96 hours. In general, the disinfection step will desirably result in a disinfected ECM hydrolysate composition having sufficiently low levels of endotoxins, viral burdens, and other contaminant materials to render it suitable for use as a fibril mass layer forming material. Endotoxin levels below about 2 endotoxin units (EUs) per gram (dry weight) are preferred, more preferably below about 1 EU per gram, as are virus levels below 100 plaque forming units per gram (dry weight), more preferably below 1 plaque forming unit per gram.

The aqueous ECM hydrolysate composition may be a substantially homogeneous solution during the dialysis step for delivering the oxidizing disinfectant to the hydrolysate composition and/or during the dialysis step for removing the oxidizing disinfectant from the hydrolysate composition.

Alternatively, the aqueous hydrolysate composition may include suspended ECM hydrolysate particles, optionally in combination with some dissolved ECM hydrolysate components, during either or both of the oxidizing disinfectant delivery and removal steps. Dialysis processes in which at least some of the ECM hydrolysate components are dissolved during the disinfectant delivery and/or removal steps are preferred and those in which substantially all of the ECM hydrolysate components are dissolved are more preferred.

The disinfection step may be conducted at any suitable temperature, and will typically be conducted between about 0° C. and about 37° C., more typically between about 4° C. and about 15° C. During this step, the concentration of the ECM hydrolysate solids in the aqueous medium may range between about 2 mg/ml and about 200 mg/ml, and may vary somewhat through the course of the dialysis due to the migration of water through the membrane. In certain embodiments, a relatively unconcentrated digest is used, having a starting ECM solids level of about 5 mg/ml to about 15 mg/ml. In other embodiments, a relatively concentrated ECM hydrolysate is used at the start of the disinfection step, for example having a concentration of at least about 20 mg/ml and up to about 200 mg/ml, more preferably at least about 100 mg/ml and up to about 200 mg/ml. It has been found that the use of concentrated ECM hydrolysates during this disinfection processing results in an ultimate gel composition having higher gel strength than that obtained using similar processing with a lower concentration ECM hydrolysate. Accordingly, processes which involve the removal of amounts of water from the ECM hydrolysate resulting from the digestion prior to the disinfection processing step are preferred. For example, such processes may include removing only a portion of the water (e.g. about 10% to about 98% by weight of the water present) prior to the dialysis/disinfection step, or may include rendering the digest to a solid by drying the material by lyophilization or otherwise, reconstituting the dried material in an aqueous medium, and then treating that aqueous medium with the dialysis/disinfection step.

In an illustrative fibrous mass layer forming material preparation embodiment, the disinfection of the aqueous medium containing the ECM hydrolysate may include adding the peroxy compound or other oxidizing disinfectant directly to the ECM hydrolysate, for example being included in an aqueous medium used to reconstitute a dried ECM hydrolysate or being added directly to an aqueous ECM hydrolysate composition. The disinfectant may then be allowed to contact the ECM hydrolysate for a sufficient period of time under suitable conditions (e.g. as described above) to disinfect the hydrolysate, and then removed from contact with the hydrolysate. In one embodiment, the oxidizing disinfectant may then be removed using a dialysis procedure as discussed above. In other embodiments, the disinfectant may be partially or completely removed using other techniques such as chromatographic or ion exchange techniques, or may be partially or completely decomposed to physiologically acceptable components. For example, when using an oxidizing disinfectant containing hydrogen peroxide (e.g. hydrogen peroxide alone or a peracid such as peracetic acid), hydrogen peroxide may be allowed or caused to decompose to water and oxygen, for example in some embodiments including the use of agents that promote the decomposition such as thermal energy or ionizing radiation, e.g. ultraviolet radiation.

In an alternative fibrous mass layer forming material preparation, the oxidizing disinfectant may be delivered into the aqueous medium containing the ECM hydrolysate by dialysis and processed sufficiently to disinfect the hydrolysate (e.g. as described above), and then removed using other techniques such as chromatographic or ion exchange techniques in whole or in part, or allowed or caused to decompose in whole or in part as discussed immediately above.

Peroxygen compounds that may be used in the disinfection step include, for example, hydrogen peroxide, organic peroxy compounds, and preferably peracids. Such disinfecting agents are used in a liquid medium, preferably a solution, having a pH of about 1.5 to about 10.0, more desirably of about 2.0 to about 6.0. As to peracid compounds that may be used, these include peracetic acid, perpropioic acid, and/or perbenzoic acid. Peracetic acid is the most preferred disinfecting agent for purposes of the present invention.

When used, peracetic acid is desirably diluted into about a 2% to about 50% by volume of alcohol solution, preferably ethanol. The concentration of the peracetic acid may range, for instance, from about 0.05% by volume to about 1.0% by volume. Most preferably, the concentration of the peracetic acid is from about 0.1% to about 0.3% by volume. When hydrogen peroxide is used, the concentration may range from about 0.05% to about 30% by volume. More desirably the hydrogen peroxide concentration is from about 1% to about 10% by volume, and most preferably from about 2% to about 5% by volume. The solution may or may not be buffered to a pH from about 5 to about 9, with more preferred pH's being from about 6 to about 7.5. These concentrations of hydrogen peroxide may be diluted in water or in an aqueous solution of about 2% to about 50% by volume of alcohol, most preferably ethanol. For additional information concerning preferred peroxy disinfecting agents useful in certain disinfecting embodiments of the present invention, reference may be made, for example, to U.S. Pat. No. 6,206,931.

In certain embodiments, flowable, ECM-based fibrous mass layer forming materials of the present invention may be prepared to have desirable properties for manufacturing, handling and use. For example, fluidized ECM hydrolysates may be prepared in an aqueous medium, which can provide a fibril mass layer of forming material. Such prepared aqueous mediums can have any suitable level of ECM hydrolysate therein. Typically, the ECM hydrolysate will be present in the aqueous medium at a concentration of about 1 mg/ml to about 200 mg/ml, more typically about 2 to about 120 mg/ml. Furthermore, flowable ECM compositions can be prepared so that in addition to neutralization, heating to physiologic temperatures (such as 37° C.) will substantially reduce the gelling time of the material.

In the formation of medical graft materials of the invention, the liquid or otherwise flowable composition containing solubilized ECM components may be applied to the substrate material in any suitable fashion. For example, an amount of an ECM or other base sheet material may be spread, potentially within a mold, cast, or other structure for retaining and/or shaping the liquid composition to be applied. The flowable composition may then be added to the surface of the ECM or other base sheet material to a desired thickness or depth. In certain embodiments as discussed above, the flowable composition will be capable of forming a gel. This gel or other liquid-containing composition may then be dried to form a dried cake or mass that includes fibrous collagen derived from the ECM material, desirably along with one or more bioactive components native to the ECM material, as discussed above.

Bismuth Thiols

Bismuth thiols of the present invention are designed to promote wound healing by preventing, reducing or eliminating biofilm development in the wound. Bismuth thiols include a group of biocidal agents having potent, broad spectrum antibacterial activity (Domenico et al., Antimicrob. Agents Chemother., vol. 41, pp. 1697-1703 (1997); and Domenico et al., Antimicrob. Agents Chemother., vol. 45, pp. 1417-1421 (2001). Bismuth thiols as used herein may also exhibit certain antifungal properties as well.

Exemplary bismuth thiols include bismuth-1,2-ethanedithiol, bismuth-2-mercaptoethanol, bismuth-3,4-dimercaptotoluene, bismuth-pyrithione, bismuth-2,3-dimercaptopropanol, bismuth-1,3-propanedithiol, bismuth-dithiothreitol, bismuth-3-mercapto-2-butanol. Additional bismuth thiols are described in U.S. Pat. No. 6,086,921, which is incorporated by reference herein. Preferably, the bismuth thiol is a bismuth dithiol. In a particularly preferred embodiment, the bismuth thiol is bismuth-1,2-ethanedithiol.

Bismuth thiols are incorporated into the bioremodelable material in an amount sufficient to prevent or reduce biofilm formation, prevent or reduce biofilm growth, or to remove or disrupt an existing bacterial biofilm. Bismuth thiol amounts may be varied depending on the efficacy of the agent in accordance with, for example, U.S. Pat. No. 6,380,248 and Domenico et al., Antimicrob. Agents Chemother., Vol. 45, No. 5, pp. 1417-1421, 2001.

Other Biofilm-Inhibiting Agents

In accordance with the present invention, the wound dressing or other medical product may further comprise at least other biofilm-inhibiting agent. The other biofilm-inhibiting agents include iron-sequestering glycoproteins, such as lactoferrin, ovotransferrin, and serrotransferrin; xylitol; chelating agents, such as EDTA, EGTA, and DTPA; biocidal agents, antibiotics, quorum sensing inhibitors, and surfactants. The other biofilm-inhibiting agent(s) may be administered with the bismuth thiol or may be administered separately. Generally, these biofilm-inhibiting agents will have minimal adverse effects on host cells in e.g., a wound bed area. Among the other biofilm-inhibiting agents, lactoferrin, xylitol, and/or antibiotics are preferred agents for use in the present invention.

The use multiple biofilm-inhibiting agents acting though multiply distinct mechanisms affecting biofilm formation and maintenance can provide synergistic effects with regard to biofilm management and wound healing. For example, biofilm-inhibiting agents can be selected to include antibiotics or biocides killing microbes, as well as agents affecting attachment to wound bed surfaces, cell-cell communication (e.g., quorum sensing) between microorganisms in the biofilm, and/or biofilm structural organization.

Lactoferrin is naturally present in human secretions (saliva, tears, mucous, milk) and constitutes an important part of a host's natural immunity to microorganisms. In addition to sequestering iron, an essential bacterial nutrient, lactoferrin also acts as a serine protease inducing degradation of bacterial secreted proteins necessary for attachment. Moreover, lactoferrin has bactericidal activity reflected in its ability to bind to gram-negative bacterial lipopolysaccharide (LPS) portions, increasing their outer membrane permeability, and leading to bacterial cell death. Lactoferrin is also known to enhance the bacterial cell killing ability of activated neutrophils.

Xylitol is a sugar alcohol naturally occurring in certain plants, has been shown to be active in blocking adhesion of pathogenic gram-positive bacteria to host surfaces and in treating biofilm-based diseases of skin and dental plaque.

Representative biocidal agents for use in the present invention include iodine compounds and derivatives thereof, such as cadexomer iodine and povidone iodine (PVP-I); silver compounds and derivatives thereof, such as silver sulfadiazine (brand names: Silvadene, SSD, SSD AF1 Thermazene) and silver nitrate ($AgNO_3$); divalent metal chelating agents, such as EDTA and EGTA; salicylic acid; chlorine dioxide; isothiazolone, derivatives thereof, compounds having isothiazolone functions, 3-isothiazolone, 5-chloro-2-methyl-3-isothiazolone, 1-methyl-3,5,7-triaza-1-azoniatricyclo (3.3.1.1) deoane chloride, 4,5-dichloro-2-octyl-3 isothiazolone, 2-bromo-2-nitropropanediol, 5-bromo-5-nitro dioxane, thiocyanomethylthiobenzothiazole, 4,5-dichloro-2-octyl-3-isothiazolone and 2n-octyl-3-isothiazolone, tetrachloroisophalonitrile, 1,2-benzisothiazolin-3-one, 2-methyl-4,5-trimethylene-4-isothiazolin-3-one, 5-chloro-2-methyl-4 isothiazolin-3-one, 2-methyl-4-isothiazolin-3-one, 4-(2-nitrobutyl)morpholine, beta-nitrostyrene ("NS"), beta-bromo-beta-nitrostyrene ("BNS"), methylchloro/isothiazolone ("IZN"), methylenebisthiocyanate ("MBT"), 2,2dibrortmo-3-nitrilopropionamide ("DBNPA"), 2-bromo-2-brornom-ethyl-glutaronitrile ("BBMGN"), alkyldimethylbenzylammoniutn chloride ("ADBAC"), and beta-tiitrovinyl furan ("NVF"), 2-methyl-3-isothiazolone, methylene bisthiocyanate, p-tolyidiiodotnethyl sulfone, 2-methylthio-4-tertbutylamino-6-cyclopropyl-amino-s-tiiazine, N,N-dimethyl-N'-phenyl-(N'fluorodiehloromethylthio)sulfa-inide, antibiotics, sulfamides, tetracycline, isothiazolone derivatives, N-(cyclo) alkyl-isothiazolone, benzisothiazolin-3-one, and mixtures of the foregoing.

Other examples of biocidal agents that may be combined with one or more of biofilm-inhibiting compounds listed above include bicyclic oxazolidoines and their mixtures, amine-based bactericide, polyacrolein copolymer, 4,4-dimethyloxazolidine, 2((hydroxymethyl)-amino) ethanol, mixtures of 1,2-benzisothiazolone-3-one with one or more amines, tetrahydro-3,5-dimethyl-2H-1,3,5-thiadiazitie-2-thione, 1,2-benzisothiazolin-3-one, tetrachloroisophthalonitrile, N-cyclopropyl-N-(1,1-dimethylethyl)-6-(methylthio)-1,3; 5-triazine-2,4-diamine, mixtures of N-cyclopropyl-N-(1, 1-dimethylethyl)-6-(methylthio)-1,3,5-triazine-2,4-diamine with tetrachloroisophthalonitrile-, mixtures of tetrachloroisophthalonitrile with 3-iodo-2-propynylbutyl carbamate, N-(trichloromethylthio)-phthalimide, 3iodo-2-propynylbutyl carbamate, tetrachloroisophthalonitrile, and mixtures of the foregoing, which are described in U.S. Application Publication No. 2006/0014285.

Non-limiting examples of antibiotics that may be used in connection with the present invention include aminopenicillins (penicillin, amoxicillin, and their congeners); cephalosporins; cycloserine; macrolides (erythromycin, clarithromycin, azithromycin, roxithromycin); quinolones; sulfonamides; rifamycins, including rifampin (RIFADIN; RIMACTANE); thienamycins (imipenem); tetracyclines (chlortetracycline, oxytetracycline, demeclocycline, methacycline, doxycycline, and minocycline); cefaclor, cefuroxime, cefprozil, chloramphenicol, ciprofloxacin, clindamycin, ethabuto, dicloxacillin, erythromycin, metronidazole, ofloxacin, griseofulvin, sulfisoxazole, griseofulvin, cephalexin, terbinafine, levofloxacin, loracarbef, nitrofurantoin, minocycline, polymyxin, vancomycin, tobramycin, clotrimazole, nystatin, ketoconazole, cefdinir, ampicillin, trimethoprim-sulfamethoxazole, itraconazole, cefixime, mebendazole, doxycycline, sparfloxacin, azithromycin, including analogs, and mixtures of the foregoing. Antibiotics are preferably selected to target microorganisms native to the wound bed. Preferably microbial target of the antibiotic is sufficiently different from its physiological counterpart to preclude adverse effects in the host cells of a subject in need of wound healing treatment.

Non-limiting examples of anti-fungal antibiotic agents include amphotericin B, flucytozine, imidazoles and triazoles, ketoconazole, itraconazole, fluconazole, ciclopirox olamine, haloprogin, tolnaftate, naftifine, terbinafine, and polyene antifungal antibiotics (nystatin).

Non-limiting examples of antiviral agents include antiretroviral agents (didanosine, stavudine, zalcidabine, zidovudine), antiherpesvirus agents (acyclovir, famciclovir, foscarnet, trifluridine, vidarabile), and other antiviral agents (amantadine, interferon alpha, ribavirin, rimantadine).

Non-limiting examples of quorum sensing antagonists include N-(3-oxododecanoyl)-L-homoserine lactone (OdDHL), N-butyrl-L-homoserine lactone (BHL), and analogs thereof.

Surfactants may be used in conjunction with other biofilm-inhibiting substances to disrupt biofilms. Previous studies have mutants defective in quorum sensing lose the ability to resist biofilm disruption in the presence of 0.2% sodium dodecyl sulfate (SDS) treatment. Non-limiting examples of surfactants include SDS; amidoalkyl betaines of fatty acids, including undecylene amidoalkyl betaine, cocamidoalkyl betaine, lauramidoalkyl betaine, and ricinolamidoalkyl betaine; Tween® 80, cyclic lipopeptide, cyclic heptapeptide, surfactin, and serrawettin.

The biofilm-inhibiting compounds or compositions of the present invention may be administered in connection with pharmaceutically acceptable carriers known to those of skill in the art.

Biofilm-inhibiting compounds or compositions may be coupled with soluble polymers as targetable carriers. This may provide controlled release of agents that may be otherwise toxic to host cells. Such polymers may include polyvinylpyrrolidone, pyran copolymer, polyhydroxypropylmethacrylamide phenyl, polyhydroxyethylaspartamidephenol, or polyethyleneoxide-polylysine substituted with palmitoyl residues. Other biodegradable polymers useful for coupling and controlled release of a biofilm-inhibiting agents include polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

Bismuth thiols and other biofilm-inhibiting agents may be formulated to provide controlled release over time, for example, days, weeks, months or years, as the ECM is degraded or eroded. In an exemplary embodiment, degradation of the ECM is modulated by an agent that decreases (e.g., via a peptide, protein, or chemical protease, such as, for example, aprotinin) or increases (e.g., a protease) the rate of degradation and/or erosion of the ECM. Alternatively, the bismuth thiols and other biofilm-inhibiting agents may comprise a microsphere composition which is attached to or incorporated within the ECM. In this embodiment, the ECM need not degrade in order to produce a time released effect of the bismuth thiols and other biofilm-inhibiting agents. Release properties can also be determined by the size and physical characteristics of the microspheres.

Bismuth thiols and other biofilm-inhibiting agents may also include, for example, adjuvants and additives, such as stabilizers, fillers, antioxidants, catalysts, plasticizers, pigments, and lubricants, to the extent such ingredients do not diminish the utility of the biofilm-inhibiting agent for its intended purpose.

Other Bioactive Agents

The wound healing process is regulated by the integrated actions of growth factors, cytokines, proteases, and extracellular matrix components (see e.g., Lobmann et al., Diabetes Care, vol. 28, no. 2, February, 2005). Chronic wounds exhibit various deficiencies and imbalances in key proteases, cytokines and growth factors. For example, poorly healing chronic wounds are typically characterized by excessive inflammation, a prolonged period of inflammation, and excessive protease activity, possibly the result of wound bed biofilms. Bacterial endotoxins, fragments of extracellular matrix, and cell detritus maintain this inflammation, which is evidenced by a large number of neutrophil granulocytes in the wound secreting various proinflammatory cytokines, particularly tumor necrosis factor-$\alpha$ (TNF-$\alpha$) and interleukin-1$\beta$ (IL-1$\beta$), which can contribute to a persistent inflammatory status. The prolonged inflammatory status contributes to the elevated protease levels, which can lead to degradation of matrix proteins and growth factors essential for healing. Indeed, as compared to acute wounds, chronic wounds typically exhibit reduced levels of growth factors, such as PDGF, b-FGF, EGF, and TGF-$\beta$, and protease regulators, including tissue inhibitors of metalloproteinases (TIMPs), such as TIMP-1. The imbalanced integration of growth factors, cytokines, proteases, and extracellular matrix components in chronic wounds can ultimately result in a failure of the wound to heal.

Accordingly, wound dressings of the present invention may further include wound healing agents and protease inhibitors as appropriate. Choice of wound healing factors may depend on whether the wound is acute or chronic.

Exemplary wound healing agents include growth factors, cytokines, and protease inhibitors. Exemplary growth factors include TGF-related growth factors (TGF-$\beta$1, TGF-$\beta$2, TGF-$\beta$3); PDGF-related growth factors (PDGF-M, PDGF-BB, VEGF); FGF-related growth factors (a-FGF, b-FGF, KGF); IGF-related growth factors (IGF-1, IGF-II, insulin); EGF-related growth factors (EGF, HB-EGF, TGF-$\alpha$, amphiregulin, betacellulin); CTGF; and combinations, analogs and/or recombinant derivatives thereof. Exemplary cytokines include proinflammatory cytokines, such as TNF-$\alpha$, IL-1, IL-2, IL-6, IL-8, $\gamma$-interferon; anti-inflammatory cytokines, such as IL-4 and IL-10; and combinations, analogs and/or recombinant derivatives thereof.

Medical products of the present invention may also include ECM sheet materials formulated to include exogenous fibronectin, as well as exogenous heparin or exogenous heparin sulfate bound thereto, and/or exogenous heparin- and heparin sulfate-binding growth factors bound to the fibronectin-bound exogenous heparin- and heparin-sulfates. Methods of making and using fibronectin-modified ECM materials are described in U.S. Provisional Application No. 60/618,965, filed Oct. 15, 2004, and in International Application Number PCT/US2005/036773, filed Oct. 14, 2005, the disclosure of which are expressly incorporated by reference herein.

Exemplary protease inhibitors include matrix metalloproteinase (MMP) inhibitors, including but not limited to TIMP-1, TIMP-2, and TIMP-3; and doxycycline, which has been shown to reduce inflammation and improve healing of chronic diabetic foot ulcers treated with a topical doxycycline gel (Lobmann et al., Diabetes Care, vol. 28, no. 2, February, 2005). MMP substrates, such as gelatin, may also be applied to the dressings of the present invention. Recent studies have shown the use of gelatin in wound dressings to reduce MMP activity and to improve healing in chronic wounds (Lobmann et al., Diabetes Care, vol. 28, no. 2, February, 2005).

Inasmuch as wounds require effective pain management, analgesics may be incorporated into the wound dressings or applied to wounds in conjunction with the wound dressings. Analgesic agents may be used for pain relief or pain suppression, especially for treatment of burns. Examples of the analgesic agents include, but are not limited to, previously mentioned nonsteroidal anti-inflammatory drugs, and opioids, such as morphine, methadone, codeine, etorphine, naloxone, and others.

Incorporation of Bioactive Agents into Bioremodelable Materials

Bismuth thiols and other biofilm-inhibiting agents, wound healing agents, and/or analgesic agents may be carried by bioremodelable sheet materials in any suitable fashion. For example, the bioactive agents may be exogenously incorporated into the carrier during their preparation or covalently attached to the carrier when preparing the wound dressing. Alternatively, bioactive agents may be added to the carrier after preparation of the carrier, for example, by impregnating (e.g., dry powder coating, soaking, coating, spraying, painting) or otherwise applying the bioactive agent(s) to the carrier using methods known to those of skill in the art.

Additionally, the exogenous bioactive agents may be applied in the form of a liquid medium containing the agent(s), such as a solution or suspension, which is contacted with all or only one or more portions of the sheet, after which the sheet can be dried to leave the agent(s) in place. Contact between the liquid medium and the sheet can be achieved in any suitable manner, including for example immersion, spraying, coating or otherwise. After drying, the drug may be substantially homogenously dispersed through the sheet, or may be selectively applied to regions of the sheet. Alternatively, the drug can be a powder which is applied, by spraying, rubbing or otherwise coating, to one or both sides of the sheet. Methods for applying bioactive agents to one or more ECM layers in monolayer or multi-layer sheet constructs are disclosed in U.S. Patent Application Publication No. US 2006/0251702, the disclosures of which are expressly incorporated by reference herein.

In another aspect, the bismuth thiols and/or other biofilm-inhibiting or wound healing agents are mixed with fluidized ECM- or other bioremodelable materials to form a substantially homogenous biofilm-inhibiting wound dressing solution. The fluidized material may be dried or formed into a gel for direct use.

Methods for Treating Wounds or Other Tissue Defects

The above-described wound dressings, graft materials or medical products may be used to treat a variety of wounds or tissue defects, including partial and full thickness wounds, diabetic ulcers, venous ulcers, chronic vascular ulcers, leg ulcers, pressure ulcers, decubitus, ulcus cruris, tunneled/undermined wounds, fistulae, surgical wounds (such as donor site wounds for autografts, post-Moh's surgery wounds, post-laser surgery wounds, wound dehiscence), hernias, trauma wounds (such as abrasions, lacerations, burns, and skin tears), draining wounds, and the like. In a preferred embodiment, a wound dressing in accordance with the present invention is used to treat a chronic wound. In other preferred embodiments, a wound dressing in accordance with the present invention is used to treat a hernia or a fistula.

The bismuth thiols and/or other biofilm-inhibiting agents may be incorporated into or onto a suitable bioremodelable source material before application to a wound or defect or may be independently applied to a wound/defect in parallel with application of the bioremodelable material. The wound dressings described herein may be utilized in conjunction with conventional wound management practices, including repeated dressing exchanges and debridement of the wound area.

For example, when preparing the wound for treatment in a conventional fashion, the physician, veterinarian or other user of the wound dressing materials of the invention may, for example, include cleaning and/or debridement of the wound with water, physiologic saline or other solutions, and potentially also treating the wound with antibiotics or other therapeutic agents. Methods for treating wounds with bioremodelable sheet constructs can be found in the manufacturer's instructions for OASIS® Wound Matrix (Cook Incorporated, West Lafayette, Ind.).

Bioremodelable sheet constructs and other dressing materials can applied to the wound in a fashion to facilitate and promote healing of the wound. In this regard, the inventive sheet constructs, for example, may be applied in a dehydrated, partially hydrated, or fully hydrated state. Once applied to a wound, the modified sheet construct will hydrate (if not previously hydrated) and remain generally in place either alone or in combination with other wound dressing materials applied below or on top of the modified ECM material.

Those skilled in the art of treating damaged or diseased tissue in humans will know or can determine optimal dosages of the biofilm-inhibiting agents for incorporation into the wound dressing to treat a subject in need. In general, the effective therapeutic amount is adjusted for body surface area requiring such treatment. A therapeutically effective amount of a biofilm-inhibiting agent in the wound dressing is expected to vary from about 0.1 milligram per kilogram of body weight per day (mg/kg/day) to about 100 mg/kg/day. Dosage determinations of biofilm-inhibiting agents may be made by a physician, veterinarian, or attending clinician. The dosages may be varied depending upon the requirements of the patient, the severity of the condition being treated and the particular agent being employed. In determining the dose, a number of factors are considered by the attending clinician, including, but not limited to: the specific tissue to be treated; pharmacodynamic characteristics of the particular agent; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment; and other relevant circumstances.

By exogenously incorporating bismuth thiols and other biofilm-inhibiting, and/or wound healing agents into the medical products of the present invention, increased biofilm inhibition, reduction, or removal can be achieved compared to conventional medical products. In addition, incorporating these agents may further enhance removal of biofilms by debridement and may reduce the necessity for repeated debridement.

For the purpose of promoting a further understanding of embodiments of the invention and their features and advantages, the following specific Examples are provided. It will be understood that these Examples are illustrative, and not limiting, in nature.

EXAMPLE 1

This Example was performed to test the antimicrobial activity of a sample of small intestinal submucosa coated with a bismuth thiol preparation.

Seven bismuth thiol compounds (50 mg each) were obtained from Microbion, Inc. (Bozeman, Mont.). These compounds included 2 preparations of bismuth-1,2-ethanedithiol (BisEDT) (Molar ratio 1:1.5), 2 preparations of bismuth-2,3-dimercaptopropanol (BisBAL) (1:1 and 1:1.5), bismuth dithioethylhritol (BisERY) (1:1.5), bismuth-3,4-dimercatotoluene (BisTOL) (1:1.5) and bismuth butane-dithiol (BisBDT) (1:1.5). Purified small intestinal submucosa (SIS) (Cook Biotech Incorporated, West Lafayette, Ind.) was made into wetted 4-layer constructs which were laminated together by lyophilization and subsequently cut into 15 mm discs (~1.76 $cm^2$) using a disc punch. Bismuth thiols were resuspended in dimethyl sulfoxide (DMSO) and diluted to appropriate concentrations for coating. Discs were coated with the bismuth thiol solutions at three final concentrations using 17.6 µl of the appropriate solution per disc for a final concentration of 1, 10, or 100 µg/$cm^2$. The discs were subsequently placed in a lyophilizer overnight to remove the DMSO solvent. Control discs were prepared using 17.6 µl of DMSO without a bismuth thiol preparation. 3 bacteria were used for this experiment: S. aureus (ATCC #25983), P. aeruginosa (ATCC #27853), and E. coli (ATCC #25922). Bacteria was grown in Tryptic Soy Broth for 16-24 hours before placing a lawn on Tryptic Soy Agar in 100 mm Petri dishes.

Sixty six samples were tested in total (7 bismuth thiol preparations 3 doses=21+1 control=22×3 bacteria=66). A lawn of one of the three bacteria investigated was swabbed onto the Tryptic Soy Agar. The bismuth thiol coated disc was placed approximately in the center of the plate and rehydrated with ~50 µl of sterile saline. Plates were incubated inverted for 24 hours at which time pictures were taken with a digital camera. Zones-of-inhibition were categorized by the approximate distance of bacterial growth inhibition from the disc edge. The effectiveness was ranked as follows: (−) for no growth retardation, (+) for growth retardation at <1 mm from disc edge, (++) for growth retardation 1-3 mm from disc edge, and (+++) for growth retardation greater than 3 mm from disc edge. Results are shown below in Tables 2-4.

TABLE 2

| Conc. (µg/$cm^2$) | Bis EDT1 | Bis EDT2 | Bis BAL1 | Bis BAL2 | Bis ERY | Bis TOL | Bis BDT |
|---|---|---|---|---|---|---|---|
| (S. aureus) | | | | | | | |
| 1 | + | ++ | + | + | − | − | − |
| 10 | ++ | ++ | +++ | +++ | ++ | + | ++ |
| 100 | +++ | +++ | +++ | +++ | +++ | + | +++ |

TABLE 3

| | | | (P. aeruginosa) | | | | |
|---|---|---|---|---|---|---|---|
| Conc. (µg/cm²) | Bis EDT1 | Bis EDT2 | Bis BAL1 | Bis BAL2 | Bis ERY | Bis TOL | Bis BDT |
| 1 | − | − | − | − | − | − | − |
| 10 | + | − | + | + | ++ | − | + |
| 100 | + | ++ | +++ | +++ | +++ | − | ++ |

TABLE 4

| | | | (E. coli) | | | | |
|---|---|---|---|---|---|---|---|
| Conc. (µg/cm²) | Bis EDT1 | Bis EDT2 | Bis BAL1 | Bis BAL2 | Bis ERY | Bis TOL | Bis BDT |
| 1 | − | − | − | − | − | − | − |
| 10 | − | + | ++ | ++ | ++ | − | ++ |
| 100 | + | + | +++ | +++ | +++ | − | ++ |

There was no zone-of-inhibition detected for the control discs. As the Tables indicate, each plate containing a disc coated with a bismuth thiol illustrated some antimicrobial activity. This suggests that bismuth thiols can be used in conjunction with a medical device to effectively retard bacterial growth on, and in the vicinity of, the medical device.

EXAMPLE 2

This Example was performed to further test the antimicrobial activity of BisERY, BisEDT, and BisBAL when coated onto a sample of small intestinal submucosa (SIS).

BisEDT (Molar ratio 1:1.5), BisBAL (1:1.5), and BisERY (1:1.5) (50 mg each) were obtained from Microbion, Inc. Small intestinal submucosa (SIS) was obtained and processed into 4-layer lyophilized sheets as described in Example 1. The sheets were subsequently cut into 15 mm discs (~1.76 cm²) using a disc punch. Bismuth thiols were resuspended in dimethyl sulfoxide (DMSO) and diluted to 0.35 µg/µl for coating. Discs were coated with the bismuth thiol solutions 50 µl of the appropriate solution per disc for a final concentration 10 µg/cm² (0.35 µg/µl*50 µl=17.5 µg/1.76 cm²=10 µg/cm²). The discs were subsequently placed in a lyophilizer overnight to remove the DMSO solvent. Control discs were prepared using 50 µl of DMSO without a bismuth thiol preparation. 3 bacteria were used for this experiment: S. aureus (ATCC #25983), P. aeruginosa (ATCC #27853), and E. coli (ATCC #25922). Bacteria was grown in Tryptic Soy Broth for 16-24 hours before placing a lawn on Tryptic Soy Agar in 100 mm Petri dishes.

Thirty samples were tested in total (3 bismuth thiol preparations @ n=3→9+1 control=10×3 bacteria=30). A lawn of one of the three bacteria investigated was swabbed onto the Tryptic Soy Agar. The bismuth thiol coated disc was rehydrated for ~5 minutes in sterile saline and placed approximately in the center of the plate. Plates were incubated inverted for 24 hours at which time pictures were taken with a digital camera. Zones-of-inhibition were measured using image analysis software (Spot RT) by determining the distance of bacterial growth inhibition from the disc edge. Results are shown below in Table 5.

TABLE 5

| Bacterial | BisEDT | BisBAL | BisERY |
|---|---|---|---|
| S. aureus | 6.83 | 7.27 | 0.80 |
| P. Aeruginosa | 2.06 | 0.16 | 0.00 |
| E. Coli | 1.28 | 1.50 | 0.00 |

There was no zone-of-inhibition detected for the control discs. As indicated in Table 5, BisERY coated discs showed a small zone-of-inhibition for S. aureus and no effect for P. aeruginosa or E. coli. BisEDT and BisBAL worked similarly for S. aureus and E. coli with BisBAL showing slightly greater zones-of-inhibition. BisEDT was more effective against P. aeruginosa than BisBAL.

This Example further demonstrates the ability of an ECM material coated with BisERY, BisEDT or BisBAL to retard bacterial growth and suggests that such compounds can be used in conjunction with a medical device for this purpose.

EXAMPLE 3

This Example was performed to test the effects of various rehydration times of an SIS disc coated with either BisEDT or BisBAL.

BisEDT (Molar ratio 1:1.5) and BisBAL (1:1.5) (50 mg each) were obtained from Microbion, Inc. Small intestinal submucosa (SIS) was obtained and processed into 4-layer lyophilized sheets as described in Example 1. The sheets were subsequently cut into 15 mm discs (~1.76 cm²) using a disc punch. Bismuth thiols were resuspended in dimethyl sulfoxide (DMSO) and diluted to appropriate concentrations for coating. Discs were coated with the bismuth thiol solutions at a final concentration of 0.35 µg/µl using 50 µl of the solution per disc for a final concentration of 10 µg/cm². The discs were subsequently placed in a lyophilizer overnight to remove the DMSO solvent. S. aureus (ATCC #25983) was used as the bacteria for this experiment. Bacteria was grown in Tryptic Soy Broth for 16-24 hours before placing a lawn on Tryptic Soy Agar in 100 mm Petri dishes.

Thirty six samples were tested in total (2 BT*n=3→6*6 rehydration times→36). A lawn of S. aureus was swabbed onto the Tryptic Soy Agar. For the 0 rehydration time point, the bismuth thiol coated disc was placed approximately in the center of the plate and rehydrated with ~50 µl of sterile saline. Other rehydration times were varied at 5, 10, 20, 30, or 60 minutes. For this, the samples were placed in sterile saline and a timer set for each time. At the appropriate time, samples were removed from the saline and placed approximately in the center of the plate. Plates were incubated inverted for 24 hours at which time pictures were taken with a digital camera. Zones-of-inhibition were compared visually between groups.

All of the BisEDT and BisBAL coated SIS discs illustrated significant effectiveness in creating a zone-of-inhibition. There were no visual differences between the rehydration time points. This suggests that a variety of rehydration times can be utilized on a medical device coated with a bismuth thiol without diminishing the antimicrobial activity of the device.

EXAMPLE 4

This Example was performed to test the compatibility of BisEDT with two sterilization techniques: ethylene oxide exposure or electron beam (E-beam) irradiation.

BisEDT was obtained from Microbion, Inc. as previously described. Small intestinal submucosa (SIS) was obtained and processed into 4-layer lyophilized sheets as described in Example 1. The sheets were subsequently cut into 15 mm discs (~1.76 cm$^2$) using a disc punch. BisEDT was resuspended in dimethyl sulfoxide (DMSO) and diluted to appropriate concentrations for coating. Discs were coated with the BisEDT solution at a final concentration of 0.35 μg/μl using 50 μl of the solution per disc for a final concentration of 10 μg/cm$^2$. The discs were subsequently placed in a lyophilizer overnight to remove the DMSO solvent. For the ethylene oxide sterilization compatibility experiment, 6 discs were coated with 10 μg/cm$^2$ BisEDT and packaged into 2 separate tyvek pouches with 3 discs per pouch. One pouch was placed in a drawer until use and left non-sterile and the other pouch was sterilized with low temperature ethylene oxide sterilization. For the E-beam sterilization, essentially the same process was performed except the discs were packaged in foil pouches and the samples were subjected to E-beam sterilization with a dose of ~25 kGy. S. aureus (ATCC #25983) was used as the bacteria for this experiment. Bacteria was grown in Tryptic Soy Broth for 16-24 hours before placing a lawn on Tryptic Soy Agar in 100 mm Petri dishes.

The experiment used a total of 6 samples (3 sterilized, 3 non-sterile) for each sterilization protocol. A lawn of S. aureus was swabbed onto the Tryptic Soy Agar. Each BisEDT coated disc was rehydrated in sterile saline for ~5 minutes then placed approximately in the center of the plate. Plates were incubated inverted for 24 hours at which time pictures were taken with a digital camera. Zones-of-inhibition were compared visually between groups.

All of the BisEDT coated SIS discs illustrated effectiveness at creating a zone-of-inhibition. E-beam sterilization exhibited greater compatibility with BisEDT than ethylene oxide sterilization.

EXAMPLE 5

This Example was performed to test the ability of BisEDT to provide anti-fungal activity.

BisEDT was obtained from Microbion, Inc. as previously described. Small intestinal submucosa (SIS) was obtained and processed into 4-layer lyophilized sheets as described in Example 1. The sheets were subsequently cut into 15 mm discs (~1.76 cm$^2$) using a disc punch. BisEDT was resuspended in dimethyl sulfoxide (DMSO) and diluted to appropriate concentrations for coating. Discs were coated with the BisEDT solution at a final concentration of 3.5 μg/μl using 50 μl of the solution per disc for a final concentration of 100 μg/cm$^2$. The discs were subsequently placed in a lyophilizer overnight to remove the DMSO solvent. A total of 6 coated discs were made—3 each for the two microorganisms investigated. These were compared against 3 uncoated controls discs cut from the same lot of SIS for each microorganism. C. albicans (ATCC #10231) and A. niger (ATCC #16404) were plated on Rose Bengal Chloramphenicol (RBC) in Petri dishes.

The experiment consisted of a total of 3 samples (3 BisEDT 100 μg/cm$^2$ coated, 3 uncoated controls) for each fungus. A lawn of either C. albicans or A. niger was swabbed onto the RBC plates. Each disc was rehydrated in sterile saline for ~5 minutes then placed approximately in the center of the plate. Plates were incubated inverted for ~48 hours for C. albicans or 5 and 8 days for A. niger at which time pictures were taken with a digital camera. Zones-of-inhibition or growth inhibition was compared visually between groups.

All of the BisEDT coated SIS discs illustrated some effectiveness at growth inhibition. For C. albicans, the BisEDT coated discs had a small zone-of-inhibition of ~1 mm from the disc edge. The uncoated controls had no zone-of-inhibition with the yeast growing to the disc edge. This indicates that the BisEDT has some, albeit minor, growth inhibiting capacity for this yeast. The mold, A. niger, did not grow in a lawn but colonies were very evident. At 5 days, the mold was able to grow over the top of the control discs. In contrast, the mold was able to grow up to the disc edge but not on the BisEDT coated disc. These plates were incubated for an additional 3 days to determine if this effect would last. Indeed, at the eight day time point, the mold was still unable to grow on the BisEDT coated discs.

This Example demonstrates that BisEDT confers some direct fungal contact growth inhibition when delivered with an ECM. BisEDT coating at 100 μg/cm$^2$ was able to inhibition growth of both a yeast, C. albicans, and a mold, A. niger.

EXAMPLE 6

This Example was performed to determine the consistency of DMSO absorption into 4-layer lyophilized SIS constructs.

Ten lots of SIS were (Cook Biotech Incorporated, West Lafayette, Ind.) obtained and each was used to prepare a 7 cm×20 cm four-layer lyophilized sheet as described in Example 1. Three 4 cm×4 cm pieces were cut from each sheet for a total of 30 samples. DMSO (Sigma Aldrich) was standard USP grade.

Each sample was weighed and weight recorded. Subsequently, each sample was placed into an excess of DMSO and allowed to absorb the fluid for 3 minutes. After 3 minutes, the sample was blotted to remove excess DMSO and weighed, with the weight recorded as final weight. DMSO content was calculated as final minus initial weight. DMSO volume was calculated as DMSO weight divided density (1.1 g/ml). Percent DMSO was calculated as DMSO weight divided by the total weight.

The processed 4-layer lyophilized SIS samples absorbed DMSO very quickly. Each piece was allowed to absorb DMSO for three minutes to give an excess of time to ensure full absorption. Initial sample weights varied from 97.6 mg to 175 mg, with an average of 134 mg and standard deviation of 19 mg. This indicates that the dry weight of individual lots of SIS can vary significantly. The final amount of DMSO absorbed varied from 416 mg to 768 mg with an average of 550 mg and standard deviation of 96 mg. This corresponds to a total volume absorbed on average of 500 mg and standard deviation of 88 mg. This analysis illustrated a significant variation on amount of DMSO absorbed for identical areas of SIS, indicating that excess volume loading with only one concentration used will likely lead to significant variation of substance absorbed onto the final device. To determine if there was a better predictor, the DMSO percent of total was calculated. This gave a result with less variation (80.2% average with 3.1% standard deviation). Results are detailed in Table 6.

TABLE 6

| Lot # | Sample | Initial Weight (mg) | Final Weight (mg) | DMSO weight (mg) | DMSO Volume (ml) | Percent DMSO |
|---|---|---|---|---|---|---|
| P107828 | a | 98 | 517 | 420 | 382 | 81.1% |
| | b | 111 | 608 | 496 | 451 | 81.7% |
| | c | 109 | 544 | 435 | 396 | 80.0% |

TABLE 6-continued

| Lot # | Sample | Initial Weight (mg) | Final Weight (mg) | DMSO weight (mg) | DMSO Volume (ml) | Percent DMSO |
|---|---|---|---|---|---|---|
| P107829 | a | 150 | 621 | 471 | 428 | 75.9% |
|  | b | 140 | 581 | 441 | 401 | 75.9% |
|  | c | 142 | 672 | 530 | 482 | 78.8% |
| P107830 | a | 130 | 674 | 544 | 495 | 80.7% |
|  | b | 141 | 628 | 487 | 443 | 77.6% |
|  | c | 138 | 676 | 538 | 489 | 79.6% |
| P107831 | a | 118 | 763 | 645 | 586 | 84.6% |
|  | b | 114 | 773 | 658 | 599 | 85.2% |
|  | c | 124 | 698 | 574 | 522 | 82.2% |
| P107832 | a | 170 | 797 | 628 | 571 | 78.7% |
|  | b | 147 | 703 | 556 | 505 | 79.1% |
|  | c | 139 | 670 | 532 | 483 | 79.3% |
| P107833 | a | 142 | 649 | 507 | 461 | 78.1% |
|  | b | 131 | 774 | 643 | 584 | 83.1% |
|  | c | 130 | 758 | 628 | 571 | 82.8% |
| P107834 | a | 165 | 740 | 574 | 522 | 77.6% |
|  | b | 122 | 537 | 415 | 377 | 77.2% |
|  | c | 139 | 647 | 509 | 462 | 78.6% |
| P107835 | a | 117 | 885 | 768 | 698 | 86.7% |
|  | b | 119 | 921 | 802 | 729 | 87.1% |
|  | c | 119 | 751 | 632 | 574 | 84.1% |
| P107836 | a | 129 | 590 | 461 | 419 | 78.2% |
|  | b | 120 | 591 | 472 | 429 | 79.8% |
|  | c | 118 | 555 | 437 | 397 | 78.7% |
| P107837 | a | 175 | 780 | 605 | 550 | 77.6% |
|  | b | 167 | 742 | 574 | 522 | 77.4% |
|  | c | 156 | 686 | 530 | 482 | 77.3% |
| Average |  | 134 | 684 | 550 | 500 | 80.2% |
| St Dev |  | 19 | 100 | 96 | 88 | 3.1% |

This Example demonstrates that DMSO is absorbed into SIS very quickly. The amount of DMSO absorbed varied for the ten lots tested. This suggests that if an excess volume of solvent is used, the ending substance absorbed will vary significantly. Thus, care must be taken if it is to be ensured that consistent bismuth thiol loading onto a medical device is achieved when DMSO is used as a solvent.

EXAMPLE 7

The Example was performed to compare the in vivo angiogenic response to SIS compared to 2 levels of BisEDT coated SIS. The model used to detect in vivo angiogenesis was the mouse subcutaneous implant method as generally described by Heeschen et al., *Nat. Med.* 200; 7:833-9.

BisEDT was obtained from Microbion, Inc. as previously described. All SIS based grafts were made from 4-layer lyophilized sheets as described in the previous Examples. Sample groups consisted of this material coated with 10 µg/cm² BisEDT or 100 µg/cm² BisEDT. Each material was cut into ten 15 mm discs. Nylon filters with 0.22 µm pores were sewn on to the top and bottom of each disc. Low temperature ethylene oxide sterilization was used for each sample.

Samples were implanted subcutaneously into the dorsal flanks of mice. After anesthesia using Ketamine (87 mg/kg) and Xylazine (13 mg/kg), a small incision was made on the posterior neck of the mouse and a dorsal subcutaneous cavity was created using blunt dissection with hemostats. This was followed by sample placement and closure of the incision with 4 interrupted stitches of 5-0 suture. Six mice per group underwent disc implantation. The implant remained in the mice for a period of 3 weeks followed by probing for capillary formation.

Mice were sacrificed using a double dose of anesthesia to ensure intact flow in vasculature. While the heart was still beating, the chest cavity was exposed, vena cava severed, and 10 ml of heparized saline injected into the left ventricle using a 23 ga butterfly infusion set to exsanguinate the mouse. After transferring syringes (while maintaining infusion needle in left ventricle), 4 ml of a fluorescent microsphere (yellow-green, 0.1 µm diameter, Molecular Probes, F-8803) suspension (1:20 dilution of stock suspension) was injected through the left ventricle resulting in perfusion of the entire vasculature. Care was taken to ensure no bubbles were introduced during the injections, as bubbles will cause micro-emboli obstructing consistent perfusion. Samples were collected with gentle dissection and gross removal of the fibrous capsule. A positive control of hind limb muscle was also collected at this point to confirm proper perfusion. Collected samples and controls were placed on ice in a closed container to maintain tissue integrity (mainly moistness). Microvasculature was imaged using a confocal microscope (Biorad), $\lambda_{ex}$=488 nm & $\lambda_{em}$=530 nm, along the edge of the samples in the area of greatest vascular infiltration. Further, vasculature of the positive controls, hind limb muscle, was imaged to confirm good perfusion.

In addition to the above, samples were collected, placed in histology cassettes, and submerged in 10% buffered formalin (Fisher). Histological sectioning and staining with hematoxilin and eosin were performed by Portland Tissue Processing. Images of H&E stained sections of the disc edge for each sample were taken using a microscrope (Olympus) with a 10× objective.

Lyophilized control SIS performed with robust angiogenesis evident burrowing multiple millimeters into the disc. Further, it was discovered that neither level of BisEDT (10 or 100 µg/cm²) coated onto the SIS affected the angiogenic potential. In addition, there were no observed symptoms of systemic toxicity, and no visual evidence of local toxicity at explant for these samples, indicating that these levels of BisEDT are well tolerated.

This Example demonstrates that both BisEDT concentration samples had similar angiogenesis and tissue ingrowth compared to control without signs of systemic or local toxicity or local inflammation. BisEDT is well tolerated and do not negatively affect remodeling of the ECM.

It is intended that the foregoing detailed description be regarded as illustrative rather than limiting, and that it be understood that it is the following claims, including all equivalents, that are intended to define the spirit and scope of this invention.

The invention claimed is:

1. A medical product comprising:
   a bismuth thiol, and
   a bioremodelable extracellular matrix material comprising a fluidized submucosal tissue having viscosity of about 2 to about 300,000 cps at 25° C.; and
   a biocompatible substrate layer adhered to the bioremodelable extracellular matrix material.

2. The medical product of claim 1, wherein the bismuth thiol is selected from the group consisting of bismuth-1,2-ethanedithiol, bismuth-2-mercaptoethanol, bismuth-3,4-dimercaptotoluene, bismuth-pyrithione, bismuth-2,3-dimercaptopropanol, bismuth-1,3-propanedithiol, bismuth-dithiothreitol, bismuth-3-mercapto-2-butanol, and mixtures thereof.

3. The medical product of claim 1, wherein the bismuth thiol is a bismuth dithiol.

4. The medical product of claim 1, wherein the bismuth dithiol is bismuth-1,2-ethanedithiol.

5. The medical product of claim 1, wherein the bioremodelable extracellular matrix material retains at least one growth factor from a source tissue.

6. The medical product of claim 5, wherein the bioremodelable extracellular matrix material is in the form of a gel.

7. The of claim 6, wherein the gel is formed from collagenous submucosal tissue material.

8. The medical product of claim 1, further comprising at least one biofilm-inhibiting agent selected from the group consisting of lactoferrin, xylitol, quorum sensing inhibitor, biocidal agent, antibiotic, surfactant, and mixtures thereof.

9. The medical product of claim 1; where the medical is a hernia repair device.

10. The medical product of claim 9, wherein the bismuth thiol is selected from the group consisting of bismuth-1,2-ethanedithiol, bismuth-2-mercaptoethanol, bismuth-3,4-dimercaptotoluene, bismuth-pyrithione, bismuth-2,3-dimercaptopropanol, bismuth-1,3-propanedithiol, bismuth-dithiothreitol, bismuth-3-mercapto-2-butanol, and mixtures thereof.

11. The medical product of claim 9, wherein the bismuth thiol is a bismuth dithiol.

12. The medical product of claim 11, wherein the bismuth dithiol is bismuth-1,2-ethanedithiol.

13. The medical product of claim 9, further comprising at least one biofilm-inhibiting agent selected from the group consisting of lactoferrin, xylitol, quorum sensing inhibitor, biocidal agent, antibiotic, surfactant, and mixtures thereof.

14. The medical product of claim 1; wherein the medical product is a bioremodelable wound dressing.

15. The medical product of claim 1, wherein the bismuth thiol is co-mixed with the bioremodelable extracellular matrix material.

16. The medical product of claim 1, wherein the bioremodelable extracellular matrix material carries bismuth thiol.

* * * * *

UNITED STATES PATENT AND TRADEMARK OFFICE
CERTIFICATE OF CORRECTION

| | | |
|---|---|---|
| PATENT NO. | : 8,343,536 B2 | Page 1 of 1 |
| APPLICATION NO. | : 12/019477 | |
| DATED | : January 1, 2013 | |
| INVENTOR(S) | : Bates et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 522 days.

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO.         : 8,343,536 B2
APPLICATION NO.    : 12/019477
DATED              : January 1, 2013
INVENTOR(S)        : Brian L. Bates et al.

Page 1 of 1

It is certified that error appears in the above-identified patent and that said Letters Patent is hereby corrected as shown below:

In the Claims

In column 39, claim 7, line 3, after "The" insert --medical product--.

In column 39, claim 9, line 9, after "product of claim 1;" replace "where the medical is a" with --wherein the medical product is a--.

Signed and Sealed this
Twenty-first Day of April, 2015

Michelle K. Lee
*Director of the United States Patent and Trademark Office*